United States Patent
Olaussen et al.

(10) Patent No.: US 9,702,875 B2
(45) Date of Patent: Jul. 11, 2017

(54) EXPRESSION OF ISOFORM 202 OF ERCC1 FOR PREDICTING RESPONSE TO CANCER CHEMOTHERAPY

(71) Applicants: Ken Olaussen, Paris (FR); Jean-Charles Soria, Paris (FR); Luc Friboulet, Le Havre (FR)

(72) Inventors: Ken Olaussen, Paris (FR); Jean-Charles Soria, Paris (FR); Luc Friboulet, Le Havre (FR)

(73) Assignee: INSTITUTE GUSTAVE-ROUSSY, Villejuif (FR)

( * ) Notice: Subject to any disclaimer, the term of this patent is extended or adjusted under 35 U.S.C. 154(b) by 0 days.

(21) Appl. No.: 14/186,285

(22) Filed: Feb. 21, 2014

(65) Prior Publication Data

US 2014/0170659 A1    Jun. 19, 2014

Related U.S. Application Data

(63) Continuation-in-part of application No. 14/021,316, filed on Sep. 9, 2013, now abandoned, and a continuation-in-part of application No. 12/282,522, filed as application No. PCT/IB2007/001538 on Mar. 14, 2007, now abandoned, application No. 14/186,285, which is a continuation-in-part of application No. 13/256,814, filed on Sep. 15, 2011, now abandoned, and a continuation-in-part of application No. 13/386,474, filed on Jan. 23, 2012, now abandoned.

(30) Foreign Application Priority Data

Mar. 14, 2006  (EP) ..................................... 06290407

(51) Int. Cl.
 *G01N 33/573*  (2006.01)
 *C12Q 1/68*  (2006.01)
 *G01N 33/574*  (2006.01)

(52) U.S. Cl.
 CPC ......... *G01N 33/573* (2013.01); *C12Q 1/6886* (2013.01); *G01N 33/57423* (2013.01); *C12Q 2600/106* (2013.01); *C12Q 2600/158* (2013.01); *G01N 2800/52* (2013.01)

(58) Field of Classification Search
 None
 See application file for complete search history.

(56) References Cited

U.S. PATENT DOCUMENTS

| | | | |
|---|---|---|---|
| 5,705,336 | A | 1/1998 | Reed et al. |
| 6,602,670 | B2 | 8/2003 | Danenberg |
| 2009/0215090 | A1 | 8/2009 | Fouret et al. |
| 2012/0004136 | A1 | 1/2012 | Fouret et al. |
| 2012/0277110 | A1 | 11/2012 | Andre et al. |

OTHER PUBLICATIONS

Online publication from American Cancer Society (ACS, types of chemotherapy drugs, Feb. 2015.*
Friboulet et al, Cell Cycle 12:3298-3306, published Mar. 2013.*
Friboulet et al, New Egnl J Med, 368:1101-1110, Mar. 21, 2013.*
Postel-Vinay et al, Oncogene 32:5377-5387, published online Aug. 12, 2013.*
Muñoz IM, Hain K, Déclais AC, Gardiner M, Toh GW, Sanchez-Pulido L, Heuckmann JM, Toth R, Macartney T, Eppink B, Kanaar R, Ponting CP, Lilley DM, Rouse J. Coordination of structure-specific nucleases by human SLX4/BTBD12 is required for DNA repair. Mol Cell. Jul. 10, 2009;35(1):116-27.
Naim V, Wilhelm T, Debatisse M, Rosselli F. ERCC1 and MUS81-EME1 promote sister chromatid separation by processing late replication intermediates at common fragile sites during mitosis. Nat Cell Biol. Jun. 30, 2013. doi: 10.1038/ncb2793.
Gurubhagavatula et al, The role of adjuvant chemotherapy for non-small cell lung caner, Semin Respir Crit Care Med vol. 26, 2006, pp. 298-303.
Rageul J, Frémin C, Ezan F, Baffet G, Langouët S. The knock-down of ERCC1 but not of XPF causes multinucleation. DNA Repair (Amst). Sep. 5, 2011;10(9):978-90.
Sargent RG, Meservy JL, Perkins BD, Kilburn AE, Intody Z, Adair GM, Nairn RS, Wilson JH. Role of the nucleotide excision repair gene ERCC1 in formation of recombination-dependent rearrangements in mammalian cells. Nucleic Acids Res. Oct. 1, 2000;28(19):3771-8.
Sijbers AM, van der Spek PJ, Odijk H, van den Berg J, van Duin M, Westerveld A, Jaspers NG, Bootsma D, Hoeijmakers JH. Mutational analysis of the human nucleotide excision repair gene ERCC1. Nucleic Acids Res. Sep. 1, 1996;24(17):3370-80. PubMed PMID: 8.
Song L, Winter AG, Selfridge J, Melton DW. A novel transcript for DNA repair gene Ercc1 in mouse skin. Transgenic Res. Feb. 2011;20(1):109-22.
Stordal B, Davey R. ERCC1 expression and RAD51B activity correlate with cell cycle response to platinum drug treatment not DNA repair. Cancer Chemother Pharmacol. Mar. 2009;63(4):661-72.
Sun Y, Li T, Ma K, Tian Z, Zhu Y, Chen F, Hu G. The impacts of ERCC1 gene exon VIII alternative splicing on cisplatin-resistance in ovarian cancer cells. Cancer Invest. Nov. 2009;27(9):891-7.
Svendsen JM, Smogorzewska A, Sowa ME, O'Connell BC, Gygi SP, Elledge SJ, Harper JW. Mammalian BTBD12/SLX4 assembles a Holliday junction resolvase and is required for DNA repair. Cell. Jul. 10, 2009;138(1):63-77.
Tan LJ, Saijo M, Kuraoka I, Narita T, Takahata C, Iwai S, Tanaka K. Xeroderma pigmentosum group F protein binds to Eg5 and is required for proper mitosis: implications for XP-F and XFE. Genes Cells. Mar. 2012;17(3):173-85.

(Continued)

Primary Examiner — Lei Yao
(74) Attorney, Agent, or Firm — Trego, Hines & Ladenheim, PLLC; Brandon Trego; Jonathan Hines

(57) ABSTRACT

An in vitro method for detecting the susceptibility of a tumor cell to a chemotherapy is disclosed. The method includes the step of measuring the expression level of the isoform 202 of the ERCC1 protein.

9 Claims, 15 Drawing Sheets

(56) References Cited

OTHER PUBLICATIONS

Usanova S, Piée-Staffa A, Sied U, Thomale J, Schneider A, Kaina B, Köberle B. Cisplatin sensitivity of testis tumour cells is due to deficiency in interstrand-crosslink repair and low ERCC1-XPF expression. Mol Cancer. Sep. 16, 2010;9:248.

van Duin M, de Wit J, Odijk H, Westerveld A, Yasui A, Koken MH, Hoeijmakers JH, Bootsma D. Molecular characterization of the human excision repair gene ERCC-1: cDNA cloning and amino acid homology with the yeast DNA repair gene RAD10. Cell. Mar. 28, 1986;44(6):913-23.

Vinciguerra P, Godinho SA, Parmar K, Pellman D, D'Andrea AD. Cytokinesis failure occurs in Fanconi anemia pathway-deficient murine and human bone marrow hematopoietic cells. J Clin Invest. Nov. 2010;120(11):3834-42.

Wang C, Lambert MW. The Fanconi anemia protein, FANCG, binds to the ERCC1-XPF endonuclease via its tetratricopeptide repeats and the central domain of ERCC1. Biochemistry. Jul. 6, 2010;49(26):5560-9. doi: 10.1021/bi100584c.

Weeda G, Donker I, de Wit J, Morreau H, Janssens R, Vissers CJ, Nigg A, van Steeg H, Bootsma D, Hoeijmakers JH. Disruption of mouse ERCC1 results in a novel repair syndrome with growth failure, nuclear abnormalities and senescence. Curr Biol. Jun. 1, 1997;7(6):427-39.

Westerveld A, Hoeijmakers JH, van Duin M, de Wit J, Odijk H, Pastink A, Wood RD, Bootsma D. Molecular cloning of a human DNA repair gene. Nature. Aug. 2-8, 1984;310(5976):425-9.

Wu Y, Mitchell TR, Zhu XD. Human XPF controls TRF2 and telomere length maintenance through distinctive mechanisms. Mech Ageing Dev. Oct. 2008;129(10):602-10.

Yu JJ, Mu C, Dabholkar M, Guo Y, Bostick-Bruton F, Reed E. Alternative splicing of ERCC1 and cisplatin-DNA adduct repair in human tumor cell lines. Int J Mol Med. Mar. 1998;1(3):617-20.

Zhu XD, Niedernhofer L, Kuster B, Mann M, Hoeijmakers JH, de Lange T. ERCC1/XPF removes the 3' overhang from uncapped telomeres and represses formation of telomeric DNA—containing double minute chromosomes. Mol Cell. Dec. 2003;12(6):1489-98.

The International Adjuvant Lung Cancer Trial Collaborative Group,Cisplatin-Based Adjuvant Chemotherapy in Patients with Completely Resected Non-Small-Cell Lung Cancer, The New England Journal of Medicine, vol. 350, 2004, pp. 351-360.

Jemal, A, et al, Cancer Statistics, CA Cancer J Clin 2005 vol. 55, 2005, pp. 10-30.

Winton et al, Vinorelbine plus Cisplatin vs. Observation in Resected Non-Small-Cell Lung Cancer, The New England Journal of Medicine, vol. 352, 2005, pp. 2589-2597.

Klee, Barbara, International Search Report for PCT/IB2007/001538, Oct. 25, 2007, EPO, NL.

Wachters et al, "ERCC1, hRad51, and BRCA1 protein expression in relation to tumor response and survival of stage ii/IV NSCLC patients treated with chemotherapy", Lung Cancer, vol. 50, pp. 211-219, Nov. 2005, Elsevier, Amsterdam, NL.

Huang Pei-Yu et al, "Correlation analysis among expression of ERCC-1, metallothionein, p53 and platinum resistance and prognosis in advanced non-small cell lung cancer", Chinese Journal of Cancer, Jul. 2004, vol. 23, No. 7 pp. 845-850.

Britten et al (Int J Cancer 89:453-457, 2000).

Dumontet (Curr Med Chem Anticancer Agent, 5:73-88, 2005, abstract only.

Olaussen et al, New Eng J. Med. 355:983-91, Sep. 2006.

Rosell et al, Semin Oncol, suppl 14 p. 37-44, 2001 provided abstract only.

Viguier et al (Clin Cancer Res 11:6212-17, Sep. 2005).

Ahmad A, Enzlin JH, Bhagwat NR, Wijgers N, Raams A, Appledoorn E, Theil AF, J Hoeijmakers JH, Vermeulen W, J Jaspers NG, Schärer OD, Niedernhofer LJ. Mislocalization of XPF-ERCC1 nuclease contributes to reduced DNA repair in XP-F patients. PLoS Genet. Mar. 5, 2010;6(3):e1000871.

Ahmad A, Robinson AR, Duensing A, van Drunen E, Beverloo HH, Weisberg DB, Hasty P, Hoeijmakers JH, Niedernhofer LJ. ERCC1-XPF endonuclease facilitates DNA double-strand break repair. Mol Cell Biol. Aug. 2008;28(16):5082-92.

Arora S, Kothandapani A, Tillison K, Kalman-Maltese V, Patrick SM. Downregulation of XPF-ERCC1 enhances cisplatin efficacy in cancer cells. DNA Repair (Amst). Jul. 1, 2010;9(7):745-53.

Belt PB, van Oosterwijk MF, Odijk H, Hoeijmakers JH, Backendorf C. Induction of a mutant phenotype in human repair proficient cells after overexpression of a mutated human DNA repair gene. Nucleic Acids Res. Oct. 25, 1991;19(20):5633-7.

Bessho T, Sancar A, Thompson LH, Thelen MP. Reconstitution of human excision nuclease with recombinant XPF-ERCC1 complex. J Biol Chem. Feb. 7, 1997;272(6):3833-7.

Chipchase MD, Melton DW. The formation of UV-induced chromosome aberrations involves ERCC1 and XPF but not other nucleotide excision repair genes. DNA Repair (Amst). Apr. 29, 2002;1(4)335-40.

Dabholkar M, Vionnet J, Bostick-Bruton F, Yu JJ, Reed E. Messenger RNA levels of XPAC and ERCC1 in ovarian cancer tissue correlate with response to platinum-based chemotherapy. J Clin Invest. Aug. 1994;94(2):703-8.

Dabholkar MD, Berger MS, Vionnet JA, Egwuagu C, Silber JR, Yu JJ, Reed E. Malignant and nonmalignant brain tissues differ in their messenger RNA expression patterns for ERCC1 and ERCC2. Cancer Res. Mar. 15, 1995;55 (6):1261-6.

De Silva IU, McHugh PJ, Clingen PH, Hartley JA. Defects in interstrand cross-link uncoupling do not account for the extreme sensitivity of ERCC1 and XPF cells to cisplatin. Nucleic Acids Res. Sep. 1, 2002;30(17):3848-56.

Fisher LA, Bessho M, Wakasugi M, Matsunaga T, Bessho T. Role of interaction of XPF with RPA in nucleotide excision repair. J Mol Biol. Oct. 21, 2011;413(2)337-46.

Friboulet L, Barrios-Gonzales D, Commo F, Olaussen KA, Vagner S, Adam J, Goubar A, Dorvault N, Lazar V, Job B, Besse B, Validire P, Girard P, Lacroix L, Hasmats J, Dufour F, André F, Soria JC. Molecular Characteristics of ERCC1-Negative versus ERCC1-Positive Tumors in Resected NSCLC. Clin Cancer Res. Sep. 1, 2011;17(17):5562-72.

Friboulet L, Olaussen KA, Pignon JP, Shepherd FA, Tsao MS, Graziano S, Kratzke R, Douillard JY, Seymour L, Pirker R, Filipits M, André F, Solary E, Ponsonnailles F, Robin A, Stoclin A, Dorvault N, Commo F, Adam J, Vanhecke E, Saulnier P, Thomale J, Le Chevalier T, Dunant A, Rousseau V, Le Teuff G, Brambilla E, Soria JC. ERCC1 isoform expression and DNA repair in non-small-cell lung cancer. N Engl J Med. Mar. 21, 2013;368(12):1101-10.

Fung MK, Han HY, Leung SC, Cheung HW, Cheung AL, Wong YC, Ling MT, Wang X. MAD2 interacts with DNA repair proteins and negatively regulates DNA damage repair. J Mol Biol. Aug. 1, 2008;381(1):24-34.

Gasior SL, Roy-Engel AM, Deininger PL. ERCC1/XPF limits L1 retrotransposition. DNA Repair (Amst). Jun. 1, 2008;7(6):983-9.

Jordheim LP, Barakat KH, Heinrich-Balard L, Matera EL, Cros-Perrial E, Bouledrak K, El Sabeh R, Perez-Pineiro R, Wishart DS, Cohen R, Tuszynski J, Dumontet C. Small Molecule Inhibitors of ERCC1-XPF Protein-Protein Interaction Synergize Alkylating Agents in Cancer Cells. Mol Pharmacol. Jul. 2013;84(1):12-24.

Lan L, Hayashi T, Rabeya RM, Nakajima S, Kanno Si, Takao M, Matsunaga T, Yoshino M, Ichikawa M, Riele Ht, Tsuchiya S, Tanaka K, Yasui A. Functional and physical interactions between ERCC1 and MSH2 complexes for resistance to cis-diamnninedichloroplatinum(II) in mammalian cells. DNA Repair (Amst). Feb. 3, 2004;3(2):135-43.

Li L, Elledge SJ, Peterson CA, Bales ES, Legerski RJ. Specific association between the human DNA repair proteins XPA and ERCC1. Proc Natl Acad Sci USA. May 24, 1994;91(11):5012-6.

Li W, Melton DW. Cisplatin regulates the MAPK kinase pathway to induce increased expression of DNA repair gene ERCC1 and increase melanoma chemoresistance. Oncogene. May 10, 2012;31(19):2412-22.

McCabe KM, Hemphill A, Akkari Y, Jakobs PM, Pauw D, Olson SB, Moses RE, Grompe M. ERCC1 is required for FANCD2 focus formation. Mol Genet Metab Sep.-Oct. 2008;95(1-2):66-73.

(56) References Cited

OTHER PUBLICATIONS

McNeil EM, Melton DW. DNA repair endonuclease ERCC1-XPF as a novel therapeutic target to overcome chemoresistance in cancer therapy. Nucleic Acids Res. Nov. 1, 2012;40(20):9990-10004.

Melton DW, Ketchen AM, Núñez F, Bonatti-Abbondandolo S, Abbondandolo A, Squires S, Johnson RT. Cells from ERCC1-deficient mice show increased genome instability and a reduced frequency of S-phase-dependent illegitimate chromosome exchange but a normal frequency of homologous recombination. J Cell Sci. Feb. 1998;111 (Pt 3):395-404.

Motycka TA, Bessho T, Post SM, Sung P, Tomkinson AE. Physical and functional interaction between the XPF/ERCC1 endonuclease and hRad52. J Biol Chem. Apr. 2, 2004;279(14):13634-9.

* cited by examiner

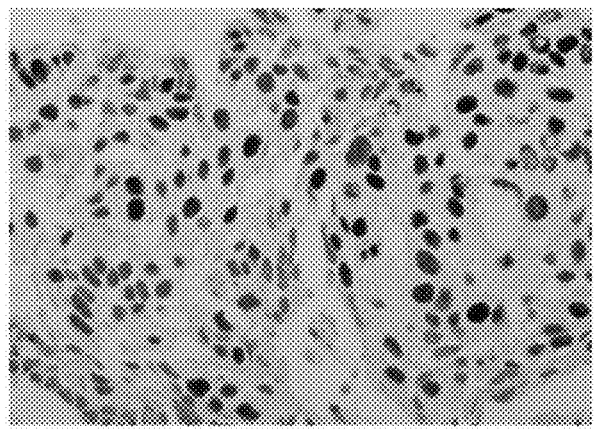
FIGURE 1A – ERCC1
POSITIVE
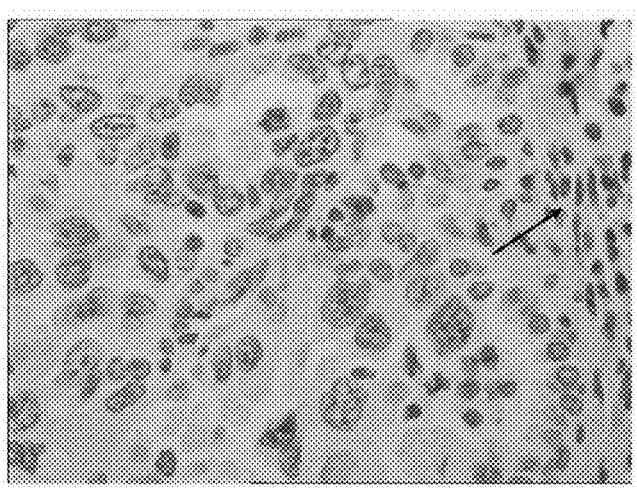
FIGURE 1B – ERCC1
NEGATIVE

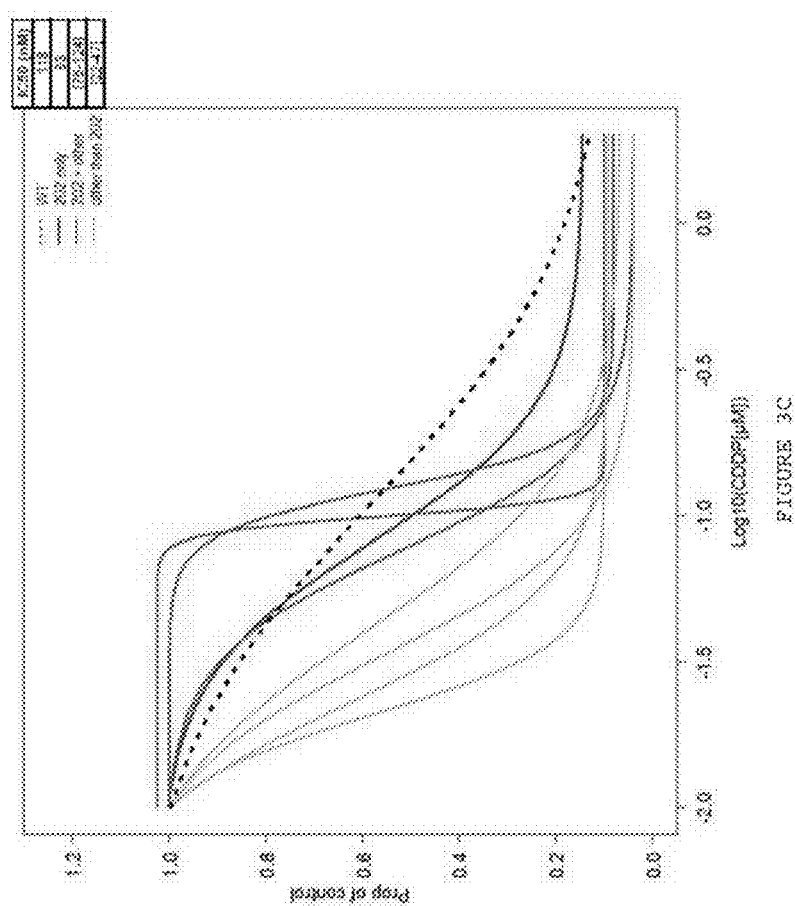

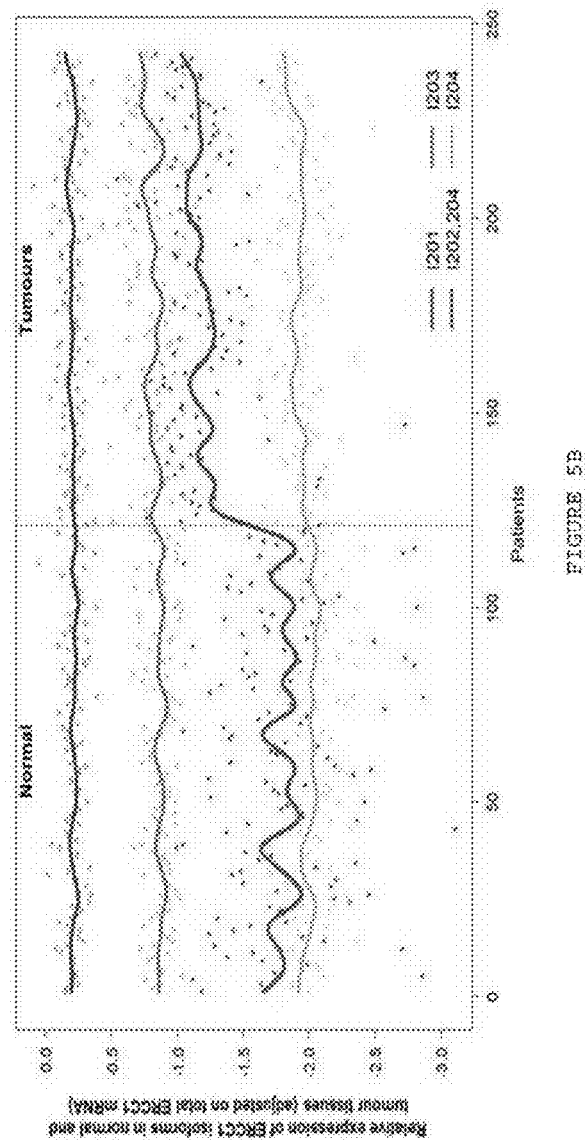

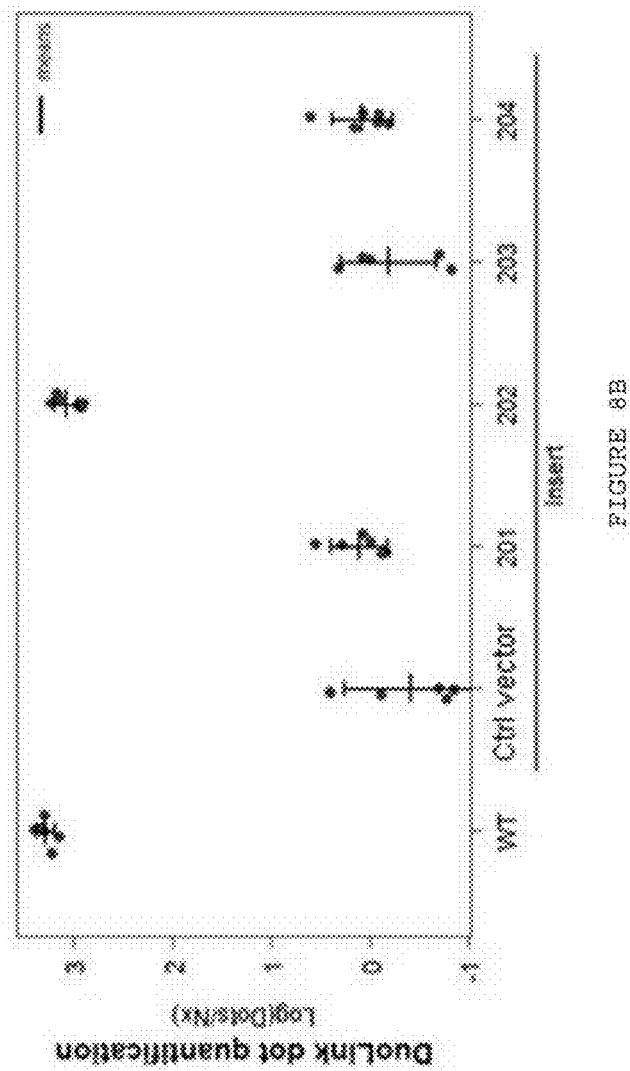

SEQUENCE LISTING

```
<160> NUMBER OF SEQ ID NOS: 17

<210> SEQ ID NO 1
<211> LENGTH: 1101
<212> TYPE: DNA
<213> ORGANISM: homo sapiens
<220> FEATURE:
<221> NAME/KEY: misc_feature
<223> OTHER INFORMATION: mRNA sequence of the ERCC1 isoform 202
      (corresponding to NM_001983.3)

<400> SEQUENCE: 1
ccggaagtgc tgcgagccct gggccacgct ggccgtgctg gcagtgggcc gcctcgatcc      60
ctctgcagtc tttcccttga ggctccaaga ccagcaggtg aggcctcgcg gcgctgaaac     120
cgtgaggccc ggaccacagg ctccagatgg accctgggaa ggacaaagag ggggtgcccc     180
agccctcagg gccgccagca aggaagaaat ttgtgatacc cctcgacgag gatgaggtcc     240
ctcctggagt ggccaagccc ttattccgat ctacacagag ccttcccact gtggacacct     300
cggcccaggc ggcccctcag acctacgccg aatatgccat ctcacagcct ctggaagggg     360
ctggggccac gtgccccaca gggtcagagc ccctggcagg agagacgccc aaccaggccc     420
tgaaacccgg ggcaaaatcc aacagcatca ttgtgagccc tcggcagagg ggcaatcccg     480
tactgaagtt cgtgcgcaat gtgccctggg aatttggcga cgtaattccc gactatgtgc     540
```

```
tgggccagag cacctgtgcc ctgttcctca gcctccgcta ccacaacctg cacccagact    600
acatccatgg gcggctgcag agcctgggga agaacttcgc cttgcgggtc ctgcttgtcc    660
aggtggatgt gaaagatccc cagcaggccc tcaaggagct ggctaagatg tgtatcctgg    720
ccgactgcac attgatcctc gcctggagcc ccgaggaagc tgggcggtac ctggagacct    780
acaaggccta tgagcagaaa ccagcggacc tcctgatgga gaagctagag caggacttcg    840
tctcccgggt gactgaatgt ctgaccaccg tgaagtcagt caacaaaacg gacagtcaga    900
ccctcctgac cacatttgga tctctggaac agctcatcgc cgcatcaaga gaagatctgg    960
ccttatgccc aggcctgggc cctcagaaag cccggaggct gtttgatgtc ctgcacgagc   1020
ccttcttgaa agtaccctga tgaccccagc tgccaaggaa accccagtg taataataaa   1080 tcgtcctccc aggccaggct c                                            1101
```

<210> SEQ ID NO 2
<211> LENGTH: 297
<212> TYPE: PRT
<213> ORGANISM: homo sapiens
<220> FEATURE:
<221> NAME/KEY: MISC_FEATURE
<223> OTHER INFORMATION: amino acid sequence of the ERCC1 isoform 202
      (corresponding to NP_001974.1)

<400> SEQUENCE: 2

```
Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Glu Val Pro
                20                  25                  30

Pro Gly Val Ala Lys Pro Leu Phe Arg Ser Thr Gln Ser Leu Pro Thr
            35                  40                  45

Val Asp Thr Ser Ala Gln Ala Ala Pro Gln Thr Tyr Ala Glu Tyr Ala
        50                  55                  60

Ile Ser Gln Pro Leu Glu Gly Ala Gly Ala Thr Cys Pro Thr Gly Ser
65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
    130                 135                 140

Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
            180                 185                 190

Asp Cys Thr Leu Ile Leu Ala Trp Ser Pro Glu Glu Ala Gly Arg Tyr
        195                 200                 205

Leu Glu Thr Tyr Lys Ala Tyr Glu Gln Lys Pro Ala Asp Leu Leu Met
    210                 215                 220

Glu Lys Leu Glu Gln Asp Phe Val Ser Arg Val Thr Glu Cys Leu Thr
225                 230                 235                 240

Thr Val Lys Ser Val Asn Lys Thr Asp Ser Gln Thr Leu Leu Thr Thr
                245                 250                 255
```

```
Phe Gly Ser Leu Glu Gln Leu Ile Ala Ala Ser Arg Glu Asp Leu Ala
            260                 265                 270

Leu Cys Pro Gly Leu Gly Pro Gln Lys Ala Arg Arg Leu Phe Asp Val
        275                 280                 285

Leu His Glu Pro Phe Leu Lys Val Pro
        290                 295

<210> SEQ ID NO 3
<211> LENGTH: 1255
<212> TYPE: DNA
<213> ORGANISM: homo sapiens
<220> FEATURE:
<221> NAME/KEY: misc_feature
<223> OTHER INFORMATION: mRNA sequence of the ERCC1 isoform 201
      (corresponding to NM_202001.2)

<400> SEQUENCE: 3 aaagggcgt  ggcgttacag  agcctctagc  gctgggtgtt  ggggacctga  cgctatggag      60
ctctcggagt  tttgtggggg  acggctgtga  gtgggggggt  cctgctgcgg  gatgagaacg    120
tagacgccag  tggctcactc  gctcctggca  ccttcccttt  caggctccag  atggaccctg    180
ggaaggacaa  agaggggggtg  ccccagccct  caggggccgcc  agcaaggaag  aaatttgtga   240 taccccctcga  cgaggatgag  gtccctcctg  gagtggccaa  gcccttattc  cgatctacac   300
agagccttcc  cactgtggac  acctcggccc  aggcggcccc  tcagacctac  gccgaatatg   360
ccatctcaca  gcctctggaa  ggggctgggg  ccacgtgccc  cacagggtca  gagcccctgg   420
caggagagac  gcccaaccag  gccctgaaac  ccggggcaaa  atccaacagc  atcattgtga   480
gccctcggca  gaggggcaat  cccgtactga  agttcgtgcg  caatgtgccc  tgggaatttg   540
gcgacgtaat  tcccgactat  gtgctgggcc  agagcacctg  tgccctgttc  ctcagcctcc   600
gctaccacaa  cctgcaccca  gactacatcc  atgggcggct  gcagagcctg  gggaagaact   660
tcgccttgcg  ggtcctgctt  gtccaggtgg  atgtgaaaga  tccccagcag  gccctcaagg   720
agctggctaa  gatgtgtatc  ctggccgact  gcacattgat  cctcgcctgg  agccccgagg   780
aagctgggcg  gtacctggag  acctacaagg  cctatgagca  gaaaccagcg  gacctcctga   840
tggagaagct  agagcaggac  ttcgtctccc  gggtgactga  atgtctgacc  accgtgaagt   900
cagtcaacaa  aacggacagt  cagaccctcc  tgaccacatt  tggatctctg  aacagctca    960 tcgccgcatc  aagagaagat  ctggccttat  gcccaggcct  gggccctcag  aaagtaagag   1020
ctctgggaaa  gaacccaagg  agttggggga  aggagagagc  cccaaataaa  cacaacctga   1080
gaccccaaag  ttttaaggtg  aaaaaagaac  caaagaccag  acacagtggc  ttccgcctgt   1140
aatcccaaca  ttttgggagg  ccaaggcggg  aggactgctt  gaggccagaa  gttggagacc   1200
agcctgggca  agtggacacc  tcatttttac  taaaaataaa  aaaactagc  tgggc         1255

<210> SEQ ID NO 4
<211> LENGTH: 323
<212> TYPE: PRT
<213> ORGANISM: homo sapiens
<220> FEATURE:
<221> NAME/KEY: MISC_FEATURE
<223> OTHER INFORMATION: amino acid sequence of the ERCC1 isoform 201
      (corresponding to NP_973730.1)

<400> SEQUENCE: 4

Met Asp Pro Gly Lys Asp Lys Glu Gly Val Pro Gln Pro Ser Gly Pro
1               5                   10                  15
```

```
Pro Ala Arg Lys Lys Phe Val Ile Pro Leu Asp Glu Asp Glu Val Pro
            20                  25                  30

Pro Gly Val Ala Lys Pro Leu Phe Arg Ser Thr Gln Ser Leu Pro Thr
        35                  40                  45

Val Asp Thr Ser Ala Gln Ala Ala Pro Gln Thr Tyr Ala Glu Tyr Ala
 50                  55                  60

Ile Ser Gln Pro Leu Glu Gly Ala Gly Ala Thr Cys Pro Thr Gly Ser
 65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
130                 135                 140

Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
            180                 185                 190

Asp Cys Thr Leu Ile Leu Ala Trp Ser Pro Glu Glu Ala Gly Arg Tyr
        195                 200                 205

Leu Glu Thr Tyr Lys Ala Tyr Glu Gln Lys Pro Ala Asp Leu Leu Met
210                 215                 220

Glu Lys Leu Glu Gln Asp Phe Val Ser Arg Val Thr Glu Cys Leu Thr
225                 230                 235                 240

Thr Val Lys Ser Val Asn Lys Thr Asp Ser Gln Thr Leu Leu Thr Thr
                245                 250                 255

Phe Gly Ser Leu Glu Gln Leu Ile Ala Ala Ser Arg Glu Asp Leu Ala
            260                 265                 270

Leu Cys Pro Gly Leu Gly Pro Gln Lys Val Arg Ala Leu Gly Lys Asn
        275                 280                 285

Pro Arg Ser Trp Gly Lys Glu Arg Ala Pro Asn Lys His Asn Leu Arg
290                 295                 300

Pro Gln Ser Phe Lys Val Lys Lys Glu Pro Lys Thr Arg His Ser Gly
305                 310                 315                 320

Phe Arg Leu

<210> SEQ ID NO 5
<211> LENGTH: 960
<212> TYPE: DNA
<213> ORGANISM: homo sapiens
<220> FEATURE:
<221> NAME/KEY: misc_feature
<223> OTHER INFORMATION: mRNA sequence of the ERCC1 isoform 203
      (corresponding to NM_001166049.1)

<400> SEQUENCE: 5
tggcagtggg ccgcctcgat ccctctgcag tctttccctt gaggctccaa gaccagcagg     60
tgaggcctcg cggcgctgaa accgtgaggc ccggaccaca ggctccagat ggaccctggg    120
aaggacaaag agggggtgcc ccagccctca gggccgccag caaggaagaa atttgtgata    180
cccctcgacg aggatgaggt ccctcctgga gtggccaagc ccttattccg atctacacag    240
```

-continued

```
agccttccca ctgtggacac ctcggcccag gcggcccctc agacctacgc cgaatatgcc    300
atctcacagc ctctggaagg ggctggggcc acgtgcccca cagggtcaga gcccctggca    360
ggagagacgc ccaaccaggc cctgaaaccc ggggcaaaat ccaacagcat cattgtgagc    420
cctcggcaga gggcaatcc cgtactgaag ttcgtgcgca atgtgccctg gaatttggc     480
gacgtaattc ccgactatgt gctgggccag agcacctgtg ccctgttcct cagcctccgc    540
taccacaacc tgcacccaga ctacatccat gggcggctgc agagcctggg gaagaacttc    600
gccttgcggg tcctgcttgt ccaggtggat gtgaaagatc cccagcaggc cctcaaggag    660
ctggctaaga tgtgtatcct ggccgactgc acattgatcc tcgcctggag ccccgaggaa    720
gctgggcggt acctggagac ctacaaggcc tatgagcaga aaccagcgga cctcctgatg    780
gagaagctag agcaggactt cgtctcccgg tctctggaac agctcatcgc cgcatcaaga    840
gaagatctgg ccttatgccc aggcctgggc cctcagaaag cccggaggct gtttgatgtc    900
ctgcacgagc ccttcttgaa agtaccctga tgaccccagc tgccaaggaa accccccagtg   960
```

<210> SEQ ID NO 6
<211> LENGTH: 273
<212> TYPE: PRT
<213> ORGANISM: homo sapiens
<220> FEATURE:
<221> NAME/KEY: MISC_FEATURE
<223> OTHER INFORMATION: amino acid sequence of the ERCC1 isoform 203
      (corresponding to NP_001159521.1)

<400> SEQUENCE: 6

```
Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Glu Val Pro
            20                  25                  30

Pro Gly Val Ala Lys Pro Leu Phe Arg Ser Thr Gln Ser Leu Pro Thr
        35                  40                  45

Val Asp Thr Ser Ala Gln Ala Ala Pro Gln Thr Tyr Ala Glu Tyr Ala
    50                  55                  60

Ile Ser Gln Pro Leu Glu Gly Ala Gly Ala Thr Cys Pro Thr Gly Ser
65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
    130                 135                 140

Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
            180                 185                 190

Asp Cys Thr Leu Ile Leu Ala Trp Ser Pro Glu Glu Ala Gly Arg Tyr
        195                 200                 205

Leu Glu Thr Tyr Lys Ala Tyr Glu Gln Lys Pro Ala Asp Leu Leu Met
    210                 215                 220

Glu Lys Leu Glu Gln Asp Phe Val Ser Arg Ser Leu Glu Gln Leu Ile
```

```
                225                 230                 235                 240

Ala Ala Ser Arg Glu Asp Leu Ala Leu Cys Pro Gly Leu Gly Pro Gln
                245                 250                 255

Lys Ala Arg Arg Leu Phe Asp Val Leu His Glu Pro Phe Leu Lys Val
                260                 265                 270

Pro

<210> SEQ ID NO 7
<211> LENGTH: 816
<212> TYPE: DNA
<213> ORGANISM: homo sapiens
<220> FEATURE:
<221> NAME/KEY: misc_feature
<223> OTHER INFORMATION: mRNA sequence of the ERCC1 isoform 204
      (corresponding to ENST00000423698.2)

<400> SEQUENCE: 7
tggcagtggg ccgcctcgat ccctctgcag tctttccctt gaggctccaa gaccagcagg    60
tgaggcctcg cggcgctgaa accgtgaggc ccggaccaca ggctccagat ggaccctggg   120
aaggacaaag aggggggtgcc ccagccctca gggccgccag caaggaagaa atttgtgata  180
cccctcgacg aggatgaggt ccctcctgga gtgaggggca atcccgtact gaagttcgtg   240
cgcaatgtgc cctgggaatt tggcgacgta attcccgact atgtgctggg ccagagcacc   300
tgtgccctgt tcctcagcct ccgctaccac aacctgcacc cagactacat ccatgggcgg   360
ctgcagagcc tggggaagaa cttcgccttg cgggtcctgc ttgtccaggt ggatgtgaaa   420
gatccccagc aggccctcaa ggagctggct aagatgtgta tcctggccga ctgcacattg   480
atcctcgcct ggagccccga ggaagctggg cggtacctgg agacctacaa ggcctatgag   540
cagaaaccag cggacctcct gatggagaag ctagagcagg acttcgtctc ccgggtgact   600
gaatgtctga ccaccgtgaa gtcagtcaac aaaacggaca gtcagaccct cctgaccaca   660
tttggatctc tggaacagct catcgccgca tcaagagaag atctggcctt atgcccaggc   720
ctgggccctc agaaagcccg gaggctgttt gatgtcctgc acgagccctt cttgaaagta   780
ccctgatgac cccagctgcc aaggaaaccc ccagtg                              816

<210> SEQ ID NO 8
<211> LENGTH: 225
<212> TYPE: PRT
<213> ORGANISM: homo sapiens
<220> FEATURE:
<221> NAME/KEY: MISC_FEATURE
<223> OTHER INFORMATION: amino acid sequence of the ERCC1 isoform 204
      (corresponding to NSP00000394875.2)

<400> SEQUENCE: 8

Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Glu Val Pro
                20                  25                  30

Pro Gly Val Arg Gly Asn Pro Val Leu Lys Phe Val Arg Asn Val Pro
            35                  40                  45

Trp Glu Phe Gly Asp Val Ile Pro Asp Tyr Val Leu Gly Gln Ser Thr
    50                  55                  60

Cys Ala Leu Phe Leu Ser Leu Arg Tyr His Asn Leu His Pro Asp Tyr
65                  70                  75                  80

Ile His Gly Arg Leu Gln Ser Leu Gly Lys Asn Phe Ala Leu Arg Val
                85                  90                  95
```

```
Leu Leu Val Gln Val Asp Val Lys Asp Pro Gln Gln Ala Leu Lys Glu
            100                 105                 110

Leu Ala Lys Met Cys Ile Leu Ala Asp Cys Thr Leu Ile Leu Ala Trp
            115                 120                 125

Ser Pro Glu Glu Ala Gly Arg Tyr Leu Glu Thr Tyr Lys Ala Tyr Glu
            130                 135                 140

Gln Lys Pro Ala Asp Leu Leu Met Glu Lys Leu Glu Gln Asp Phe Val
145                 150                 155                 160

Ser Arg Val Thr Glu Cys Leu Thr Thr Val Lys Ser Val Asn Lys Thr
                165                 170                 175

Asp Ser Gln Thr Leu Leu Thr Thr Phe Gly Ser Leu Glu Gln Leu Ile
            180                 185                 190

Ala Ala Ser Arg Glu Asp Leu Ala Leu Cys Pro Gly Leu Gly Pro Gln
            195                 200                 205

Lys Ala Arg Arg Leu Phe Asp Val Leu His Glu Pro Phe Leu Lys Val
            210                 215                 220

Pro
225

<210> SEQ ID NO 9
<211> LENGTH: 916
<212> TYPE: PRT
<213> ORGANISM: homo sapiens
<220> FEATURE:
<221> NAME/KEY: MISC_FEATURE
<223> OTHER INFORMATION: amino acid sequence of the XPF protein
      (corresponding to NP_005227.1). (Note: the official symbol of the
      corresponding coding gene is ERCC4).

<400> SEQUENCE: 9

Met Glu Ser Gly Gln Pro Ala Arg Arg Ile Ala Met Ala Pro Leu Leu
1               5                   10                  15

Glu Tyr Glu Arg Gln Leu Val Leu Glu Leu Leu Asp Thr Asp Gly Leu
            20                  25                  30

Val Val Cys Ala Arg Gly Leu Gly Ala Asp Arg Leu Leu Tyr His Phe
        35                  40                  45

Leu Gln Leu His Cys His Pro Ala Cys Leu Val Leu Val Leu Asn Thr
50                  55                  60

Gln Pro Ala Glu Glu Glu Tyr Phe Ile Asn Gln Leu Lys Ile Glu Gly
65                  70                  75                  80

Val Glu His Leu Pro Arg Arg Val Thr Asn Glu Ile Thr Ser Asn Ser
                85                  90                  95

Arg Tyr Glu Val Tyr Thr Gln Gly Gly Val Ile Phe Ala Thr Ser Arg
            100                 105                 110

Ile Leu Val Val Asp Phe Leu Thr Asp Arg Ile Pro Ser Asp Leu Ile
            115                 120                 125

Thr Gly Ile Leu Val Tyr Arg Ala His Arg Ile Ile Glu Ser Cys Gln
            130                 135                 140

Glu Ala Phe Ile Leu Arg Leu Phe Arg Gln Lys Asn Lys Arg Gly Phe
145                 150                 155                 160

Ile Lys Ala Phe Thr Asp Asn Ala Val Ala Phe Asp Thr Gly Phe Cys
                165                 170                 175

His Val Glu Arg Val Met Arg Asn Leu Phe Val Arg Lys Leu Tyr Leu
            180                 185                 190

Trp Pro Arg Phe His Val Ala Val Asn Ser Phe Leu Glu Gln His Lys
            195                 200                 205
```

```
Pro Glu Val Val Glu Ile His Val Ser Met Thr Pro Thr Met Leu Ala
    210                 215                 220

Ile Gln Thr Ala Ile Leu Asp Ile Leu Asn Ala Cys Leu Lys Glu Leu
225                 230                 235                 240

Lys Cys His Asn Pro Ser Leu Glu Val Glu Asp Leu Ser Leu Glu Asn
                245                 250                 255

Ala Ile Gly Lys Pro Phe Asp Lys Thr Ile Arg His Tyr Leu Asp Pro
            260                 265                 270

Leu Trp His Gln Leu Gly Ala Lys Thr Lys Ser Leu Val Gln Asp Leu
        275                 280                 285

Lys Ile Leu Arg Thr Leu Gln Tyr Leu Ser Gln Tyr Asp Cys Val
290                 295                 300

Thr Phe Leu Asn Leu Leu Glu Ser Leu Arg Ala Thr Glu Lys Ala Phe
305                 310                 315                 320

Gly Gln Asn Ser Gly Trp Leu Phe Leu Asp Ser Ser Thr Ser Met Phe
                325                 330                 335

Ile Asn Ala Arg Ala Arg Val Tyr His Leu Pro Asp Ala Lys Met Ser
            340                 345                 350

Lys Lys Glu Lys Ile Ser Glu Lys Met Glu Ile Lys Glu Gly Glu Glu
        355                 360                 365

Thr Lys Lys Glu Leu Val Leu Glu Ser Asn Pro Lys Trp Glu Ala Leu
370                 375                 380

Thr Glu Val Leu Lys Glu Ile Glu Ala Glu Asn Lys Glu Ser Glu Ala
385                 390                 395                 400

Leu Gly Gly Pro Gly Gln Val Leu Ile Cys Ala Ser Asp Asp Arg Thr
                405                 410                 415

Cys Ser Gln Leu Arg Asp Tyr Ile Thr Leu Gly Ala Glu Ala Phe Leu
            420                 425                 430

Leu Arg Leu Tyr Arg Lys Thr Phe Glu Lys Asp Ser Lys Ala Glu Glu
        435                 440                 445

Val Trp Met Lys Phe Arg Lys Glu Asp Ser Ser Lys Arg Ile Arg Lys
450                 455                 460

Ser His Lys Arg Pro Lys Asp Pro Gln Asn Lys Glu Arg Ala Ser Thr
465                 470                 475                 480

Lys Glu Arg Thr Leu Lys Lys Lys Arg Lys Leu Thr Leu Thr Gln
                485                 490                 495

Met Val Gly Lys Pro Glu Glu Leu Glu Glu Gly Asp Val Glu Glu
            500                 505                 510

Gly Tyr Arg Arg Glu Ile Ser Ser Pro Glu Ser Cys Pro Glu Glu
        515                 520                 525

Ile Lys His Glu Glu Phe Asp Val Asn Leu Ser Ser Asp Ala Ala Phe
530                 535                 540

Gly Ile Leu Lys Glu Pro Leu Thr Ile Ile His Pro Leu Leu Gly Cys
545                 550                 555                 560

Ser Asp Pro Tyr Ala Leu Thr Arg Val Leu His Glu Val Glu Pro Arg
                565                 570                 575

Tyr Val Leu Tyr Asp Ala Glu Leu Thr Phe Val Arg Gln Leu Glu
            580                 585                 590

Ile Tyr Arg Ala Ser Arg Pro Gly Lys Pro Leu Arg Val Tyr Phe Leu
        595                 600                 605

Ile Tyr Gly Gly Ser Thr Glu Glu Gln Arg Tyr Leu Thr Ala Leu Arg
610                 615                 620
```

```
Lys Glu Lys Glu Ala Phe Glu Lys Leu Ile Arg Glu Lys Ala Ser Met
625                 630                 635                 640

Val Val Pro Glu Arg Glu Gly Arg Asp Glu Thr Asn Leu Asp Leu
            645                 650                 655

Val Arg Gly Thr Ala Ser Ala Asp Val Ser Thr Asp Thr Arg Lys Ala
                660                 665                 670

Gly Gly Gln Glu Gln Asn Gly Thr Gln Gln Ser Ile Val Val Asp Met
            675                 680                 685

Arg Glu Phe Arg Ser Glu Leu Pro Ser Leu Ile His Arg Arg Gly Ile
690                 695                 700

Asp Ile Glu Pro Val Thr Leu Glu Val Gly Asp Tyr Ile Leu Thr Pro
705                 710                 715                 720

Glu Met Cys Val Glu Arg Lys Ser Ile Ser Asp Leu Ile Gly Ser Leu
                725                 730                 735

Asn Asn Gly Arg Leu Tyr Ser Gln Cys Ile Ser Met Ser Arg Tyr Tyr
                740                 745                 750

Lys Arg Pro Val Leu Leu Ile Glu Phe Asp Pro Ser Lys Pro Phe Ser
            755                 760                 765

Leu Thr Ser Arg Gly Ala Leu Phe Gln Glu Ile Ser Ser Asn Asp Ile
770                 775                 780

Ser Ser Lys Leu Thr Leu Leu Thr Leu His Phe Pro Arg Leu Arg Ile
785                 790                 795                 800

Leu Trp Cys Pro Ser Pro His Ala Thr Ala Glu Leu Phe Glu Glu Leu
                805                 810                 815

Lys Gln Ser Lys Pro Gln Pro Asp Ala Ala Thr Ala Leu Ala Ile Thr
            820                 825                 830

Ala Asp Ser Glu Thr Leu Pro Glu Ser Glu Lys Tyr Asn Pro Gly Pro
            835                 840                 845

Gln Asp Phe Leu Leu Lys Met Pro Gly Val Asn Ala Lys Asn Cys Arg
            850                 855                 860

Ser Leu Met His His Val Lys Asn Ile Ala Glu Leu Ala Ala Leu Ser
865                 870                 875                 880

Gln Asp Glu Leu Thr Ser Ile Leu Gly Asn Ala Ala Asn Ala Lys Gln
                885                 890                 895

Leu Tyr Asp Phe Ile His Thr Ser Phe Ala Glu Val Val Ser Lys Gly
                900                 905                 910

Lys Gly Lys Lys
        915

<210> SEQ ID NO 10
<211> LENGTH: 273
<212> TYPE: PRT
<213> ORGANISM: homo sapiens
<220> FEATURE:
<221> NAME/KEY: MISC_FEATURE
<223> OTHER INFORMATION: amino acid sequence of the XPA protein
      (corresponding to NP_000371.1)

<400> SEQUENCE: 10

Met Ala Ala Ala Asp Gly Ala Leu Pro Glu Ala Ala Ala Leu Glu Gln
1               5                   10                  15

Pro Ala Glu Leu Pro Ala Ser Val Arg Ala Ser Ile Glu Arg Lys Arg
            20                  25                  30

Gln Arg Ala Leu Met Leu Arg Gln Ala Arg Leu Ala Ala Arg Pro Tyr
        35                  40                  45

Ser Ala Thr Ala Ala Ala Ala Thr Gly Gly Met Ala Asn Val Lys Ala
```

```
            50                  55                  60
Ala Pro Lys Ile Ile Asp Thr Gly Gly Gly Phe Ile Leu Glu Glu Glu
 65                  70                  75                  80

Glu Glu Glu Glu Gln Lys Ile Gly Lys Val Val His Gln Pro Gly Pro
                 85                  90                  95

Val Met Glu Phe Asp Tyr Val Ile Cys Glu Glu Cys Gly Lys Glu Phe
                100                 105                 110

Met Asp Ser Tyr Leu Met Asn His Phe Asp Leu Pro Thr Cys Asp Asn
                115                 120                 125

Cys Arg Asp Ala Asp Asp Lys His Lys Leu Ile Thr Lys Thr Glu Ala
            130                 135                 140

Lys Gln Glu Tyr Leu Leu Lys Asp Cys Asp Leu Glu Lys Arg Glu Pro
145                 150                 155                 160

Pro Leu Lys Phe Ile Val Lys Lys Asn Pro His His Ser Gln Trp Gly
                165                 170                 175

Asp Met Lys Leu Tyr Leu Lys Leu Gln Ile Val Lys Arg Ser Leu Glu
            180                 185                 190

Val Trp Gly Ser Gln Glu Ala Leu Glu Glu Ala Lys Glu Val Arg Gln
            195                 200                 205

Glu Asn Arg Glu Lys Met Lys Gln Lys Lys Phe Asp Lys Lys Val Lys
210                 215                 220

Glu Leu Arg Arg Ala Val Arg Ser Ser Val Trp Lys Arg Glu Thr Ile
225                 230                 235                 240

Val His Gln His Glu Tyr Gly Pro Glu Glu Asn Leu Glu Asp Asp Met
                245                 250                 255

Tyr Arg Lys Thr Cys Thr Met Cys Gly His Glu Leu Thr Tyr Glu Lys
                260                 265                 270
Met

<210> SEQ ID NO 11
<211> LENGTH: 934
<212> TYPE: PRT
<213> ORGANISM: homo sapiens
<220> FEATURE:
<221> NAME/KEY: MISC_FEATURE
<223> OTHER INFORMATION: amino acid sequence of the MSH2 isoform 1
      (corresponding to NP_000242.1)

<400> SEQUENCE: 11

Met Ala Val Gln Pro Lys Glu Thr Leu Gln Leu Glu Ser Ala Ala Glu
  1               5                  10                  15

Val Gly Phe Val Arg Phe Phe Gln Gly Met Pro Glu Lys Pro Thr Thr
                 20                  25                  30

Thr Val Arg Leu Phe Asp Arg Gly Asp Phe Tyr Thr Ala His Gly Glu
             35                  40                  45

Asp Ala Leu Leu Ala Ala Arg Glu Val Phe Lys Thr Gln Gly Val Ile
 50                  55                  60

Lys Tyr Met Gly Pro Ala Gly Ala Lys Asn Leu Gln Ser Val Val Leu
 65                  70                  75                  80

Ser Lys Met Asn Phe Glu Ser Phe Val Lys Asp Leu Leu Leu Val Arg
                 85                  90                  95

Gln Tyr Arg Val Glu Val Tyr Lys Asn Arg Ala Gly Asn Lys Ala Ser
                100                 105                 110

Lys Glu Asn Asp Trp Tyr Leu Ala Tyr Lys Ala Ser Pro Gly Asn Leu
            115                 120                 125
```

-continued

```
Ser Gln Phe Glu Asp Ile Leu Phe Gly Asn Asn Asp Met Ser Ala Ser
    130                 135                 140
Ile Gly Val Val Gly Val Lys Met Ser Ala Val Asp Gly Gln Arg Gln
145                 150                 155                 160
Val Gly Val Gly Tyr Val Asp Ser Ile Gln Arg Lys Leu Gly Leu Cys
                165                 170                 175
Glu Phe Pro Asp Asn Asp Gln Phe Ser Asn Leu Glu Ala Leu Leu Ile
            180                 185                 190
Gln Ile Gly Pro Lys Glu Cys Val Leu Pro Gly Gly Glu Thr Ala Gly
        195                 200                 205
Asp Met Gly Lys Leu Arg Gln Ile Ile Gln Arg Gly Gly Ile Leu Ile
    210                 215                 220
Thr Glu Arg Lys Lys Ala Asp Phe Ser Thr Lys Asp Ile Tyr Gln Asp
225                 230                 235                 240
Leu Asn Arg Leu Leu Lys Gly Lys Lys Gly Glu Gln Met Asn Ser Ala
                245                 250                 255
Val Leu Pro Glu Met Glu Asn Gln Val Ala Val Ser Ser Leu Ser Ala
            260                 265                 270
Val Ile Lys Phe Leu Glu Leu Leu Ser Asp Asp Ser Asn Phe Gly Gln
        275                 280                 285
Phe Glu Leu Thr Thr Phe Asp Phe Ser Gln Tyr Met Lys Leu Asp Ile
    290                 295                 300
Ala Ala Val Arg Ala Leu Asn Leu Phe Gln Gly Ser Val Glu Asp Thr
305                 310                 315                 320
Thr Gly Ser Gln Ser Leu Ala Ala Leu Leu Asn Lys Cys Lys Thr Pro
                325                 330                 335
Gln Gly Gln Arg Leu Val Asn Gln Trp Ile Lys Gln Pro Leu Met Asp
            340                 345                 350
Lys Asn Arg Ile Glu Glu Arg Leu Asn Leu Val Glu Ala Phe Val Glu
        355                 360                 365
Asp Ala Glu Leu Arg Gln Thr Leu Gln Glu Asp Leu Leu Arg Arg Phe
    370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                405                 410                 415
Val Ile Gln Ala Leu Glu Lys His Glu Gly Lys His Gln Lys Leu Leu
            420                 425                 430
Leu Ala Val Phe Val Thr Pro Leu Thr Asp Leu Arg Ser Asp Phe Ser
        435                 440                 445
Lys Phe Gln Glu Met Ile Glu Thr Thr Leu Asp Met Asp Gln Val Glu
    450                 455                 460
Asn His Glu Phe Leu Val Lys Pro Ser Phe Asp Pro Asn Leu Ser Glu
465                 470                 475                 480
Leu Arg Glu Ile Met Asn Asp Leu Glu Lys Lys Met Gln Ser Thr Leu
                485                 490                 495
Ile Ser Ala Ala Arg Asp Leu Gly Leu Asp Pro Gly Lys Gln Ile Lys
            500                 505                 510
Leu Asp Ser Ser Ala Gln Phe Gly Tyr Tyr Phe Arg Val Thr Cys Lys
        515                 520                 525
Glu Glu Lys Val Leu Arg Asn Asn Lys Asn Phe Ser Thr Val Asp Ile
    530                 535                 540
Gln Lys Asn Gly Val Lys Phe Thr Asn Ser Lys Leu Thr Ser Leu Asn
```

```
            545                 550                 555                 560
Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
                580                 585                 590

Gln Thr Leu Asn Asp Val Leu Ala Gln Leu Asp Ala Val Val Ser Phe
                595                 600                 605

Ala His Val Ser Asn Gly Ala Pro Val Pro Tyr Val Arg Pro Ala Ile
                610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                    645                 650                 655

Phe Glu Lys Asp Lys Gln Met Phe His Ile Ile Thr Gly Pro Asn Met
                660                 665                 670

Gly Gly Lys Ser Thr Tyr Ile Arg Gln Thr Gly Val Ile Val Leu Met
                675                 680                 685

Ala Gln Ile Gly Cys Phe Val Pro Cys Glu Ser Ala Glu Val Ser Ile
690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
                740                 745                 750

Gly Thr Ser Thr Tyr Asp Gly Phe Gly Leu Ala Trp Ala Ile Ser Glu
                755                 760                 765

Tyr Ile Ala Thr Lys Ile Gly Ala Phe Cys Met Phe Ala Thr His Phe
770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
                820                 825                 830

Leu Ala Asn Phe Pro Lys His Val Ile Glu Cys Ala Lys Gln Lys Ala
                835                 840                 845

Leu Glu Leu Glu Glu Phe Gln Tyr Ile Gly Glu Ser Gln Gly Tyr Asp
850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
                900                 905                 910

Ala Glu Val Ile Ala Lys Asn Asn Ser Phe Val Asn Glu Ile Ile Ser
                915                 920                 925

Arg Ile Lys Val Thr Thr
            930

<210> SEQ ID NO 12
<211> LENGTH: 868
<212> TYPE: PRT
<213> ORGANISM: homo sapiens
```

<220> FEATURE:
<221> NAME/KEY: MISC_FEATURE
<223> OTHER INFORMATION: amino acid sequence of the MSH2 isoform 2
      (corresponding to NP_001245210.1)

<400> SEQUENCE: 12

Met Gly Pro Ala Gly Ala Lys Asn Leu Gln Ser Val Val Leu Ser Lys
1               5                   10                  15

Met Asn Phe Glu Ser Phe Val Lys Asp Leu Leu Leu Val Arg Gln Tyr
            20                  25                  30

Arg Val Glu Val Tyr Lys Asn Arg Ala Gly Asn Lys Ala Ser Lys Glu
        35                  40                  45

Asn Asp Trp Tyr Leu Ala Tyr Lys Ala Ser Pro Gly Asn Leu Ser Gln
    50                  55                  60

Phe Glu Asp Ile Leu Phe Gly Asn Asn Asp Met Ser Ala Ser Ile Gly
65                  70                  75                  80

Val Val Gly Val Lys Met Ser Ala Val Asp Gly Gln Arg Gln Val Gly
                85                  90                  95

Val Gly Tyr Val Asp Ser Ile Gln Arg Lys Leu Gly Leu Cys Glu Phe
            100                 105                 110

Pro Asp Asn Asp Gln Phe Ser Asn Leu Glu Ala Leu Leu Ile Gln Ile
        115                 120                 125

Gly Pro Lys Glu Cys Val Leu Pro Gly Gly Glu Thr Ala Gly Asp Met
130                 135                 140

Gly Lys Leu Arg Gln Ile Ile Gln Arg Gly Gly Ile Leu Ile Thr Glu
145                 150                 155                 160

Arg Lys Lys Ala Asp Phe Ser Thr Lys Asp Ile Tyr Gln Asp Leu Asn
                165                 170                 175

Arg Leu Leu Lys Gly Lys Lys Gly Glu Gln Met Asn Ser Ala Val Leu
            180                 185                 190

Pro Glu Met Glu Asn Gln Val Ala Val Ser Ser Leu Ser Ala Val Ile
        195                 200                 205

Lys Phe Leu Glu Leu Leu Ser Asp Asp Ser Asn Phe Gly Gln Phe Glu
    210                 215                 220

Leu Thr Thr Phe Asp Phe Ser Gln Tyr Met Lys Leu Asp Ile Ala Ala
225                 230                 235                 240

Val Arg Ala Leu Asn Leu Phe Gln Gly Ser Val Glu Asp Thr Thr Gly
                245                 250                 255

Ser Gln Ser Leu Ala Ala Leu Leu Asn Lys Cys Lys Thr Pro Gln Gly
            260                 265                 270

Gln Arg Leu Val Asn Gln Trp Ile Lys Gln Pro Leu Met Asp Lys Asn
        275                 280                 285

Arg Ile Glu Glu Arg Leu Asn Leu Val Glu Ala Phe Val Glu Asp Ala
    290                 295                 300

Glu Leu Arg Gln Thr Leu Gln Glu Asp Leu Leu Arg Arg Phe Pro Asp
305                 310                 315                 320

Leu Asn Arg Leu Ala Lys Lys Phe Gln Arg Gln Ala Ala Asn Leu Gln
                325                 330                 335

Asp Cys Tyr Arg Leu Tyr Gln Gly Ile Asn Gln Leu Pro Asn Val Ile
            340                 345                 350

Gln Ala Leu Glu Lys His Glu Gly Lys His Gln Lys Leu Leu Leu Ala
        355                 360                 365

Val Phe Val Thr Pro Leu Thr Asp Leu Arg Ser Asp Phe Ser Lys Phe
    370                 375                 380

Gln Glu Met Ile Glu Thr Thr Leu Asp Met Asp Gln Val Glu Asn His
385                 390                 395                 400

Glu Phe Leu Val Lys Pro Ser Phe Asp Pro Asn Leu Ser Glu Leu Arg
        405                 410                 415

Glu Ile Met Asn Asp Leu Glu Lys Lys Met Gln Ser Thr Leu Ile Ser
            420                 425                 430

Ala Ala Arg Asp Leu Gly Leu Asp Pro Gly Lys Gln Ile Lys Leu Asp
        435                 440                 445

Ser Ser Ala Gln Phe Gly Tyr Tyr Phe Arg Val Thr Cys Lys Glu Glu
    450                 455                 460

Lys Val Leu Arg Asn Asn Lys Asn Phe Ser Thr Val Asp Ile Gln Lys
465                 470                 475                 480

Asn Gly Val Lys Phe Thr Asn Ser Lys Leu Thr Ser Leu Asn Glu Glu
                485                 490                 495

Tyr Thr Lys Asn Lys Thr Glu Tyr Glu Glu Ala Gln Asp Ala Ile Val
            500                 505                 510

Lys Glu Ile Val Asn Ile Ser Ser Gly Tyr Val Glu Pro Met Gln Thr
        515                 520                 525

Leu Asn Asp Val Leu Ala Gln Leu Asp Ala Val Ser Phe Ala His
    530                 535                 540

Val Ser Asn Gly Ala Pro Val Pro Tyr Val Arg Pro Ala Ile Leu Glu
545                 550                 555                 560

Lys Gly Gln Gly Arg Ile Ile Leu Lys Ala Ser Arg His Ala Cys Val
                565                 570                 575

Glu Val Gln Asp Glu Ile Ala Phe Ile Pro Asn Asp Val Tyr Phe Glu
            580                 585                 590

Lys Asp Lys Gln Met Phe His Ile Ile Thr Gly Pro Asn Met Gly Gly
        595                 600                 605

Lys Ser Thr Tyr Ile Arg Gln Thr Gly Val Ile Val Leu Met Ala Gln
    610                 615                 620

Ile Gly Cys Phe Val Pro Cys Glu Ser Ala Glu Val Ser Ile Val Asp
625                 630                 635                 640

Cys Ile Leu Ala Arg Val Gly Ala Gly Asp Ser Gln Leu Lys Gly Val
                645                 650                 655

Ser Thr Phe Met Ala Glu Met Leu Glu Thr Ala Ser Ile Leu Arg Ser
            660                 665                 670

Ala Thr Lys Asp Ser Leu Ile Ile Ile Asp Glu Leu Gly Arg Gly Thr
        675                 680                 685

Ser Thr Tyr Asp Gly Phe Gly Leu Ala Trp Ala Ile Ser Glu Tyr Ile
    690                 695                 700

Ala Thr Lys Ile Gly Ala Phe Cys Met Phe Ala Thr His Phe His Glu
705                 710                 715                 720

Leu Thr Ala Leu Ala Asn Gln Ile Pro Thr Val Asn Asn Leu His Val
                725                 730                 735

Thr Ala Leu Thr Thr Glu Glu Thr Leu Thr Met Leu Tyr Gln Val Lys
            740                 745                 750

Lys Gly Val Cys Asp Gln Ser Phe Gly Ile His Val Ala Glu Leu Ala
        755                 760                 765

Asn Phe Pro Lys His Val Ile Glu Cys Ala Lys Gln Lys Ala Leu Glu
    770                 775                 780

Leu Glu Glu Phe Gln Tyr Ile Gly Glu Ser Gln Gly Tyr Asp Ile Met
785                 790                 795                 800

Glu Pro Ala Ala Lys Lys Cys Tyr Leu Glu Arg Glu Gln Gly Glu Lys

```
                            805                 810                 815

Ile Ile Gln Glu Phe Leu Ser Lys Val Lys Gln Met Pro Phe Thr Glu
            820                 825                 830

Met Ser Glu Glu Asn Ile Thr Ile Lys Leu Lys Gln Leu Lys Ala Glu
            835                 840                 845

Val Ile Ala Lys Asn Asn Ser Phe Val Asn Glu Ile Ile Ser Arg Ile
    850                 855                 860

Lys Val Thr Thr
865

<210> SEQ ID NO 13
<211> LENGTH: 622
<212> TYPE: PRT
<213> ORGANISM: homo sapiens
<220> FEATURE:
<221> NAME/KEY: MISC_FEATURE
<223> OTHER INFORMATION: amino acid sequence of the FANCG protein
      (corresponding to NP_004620.1)

<400> SEQUENCE: 13

Met Ser Arg Gln Thr Thr Ser Val Gly Ser Ser Cys Leu Asp Leu Trp
1               5                   10                  15

Arg Glu Lys Asn Asp Arg Leu Val Arg Gln Ala Lys Val Ala Gln Asn
            20                  25                  30

Ser Gly Leu Thr Leu Arg Arg Gln Gln Leu Ala Gln Asp Ala Leu Glu
        35                  40                  45

Gly Leu Arg Gly Leu Leu His Ser Leu Gln Gly Leu Pro Ala Ala Val
    50                  55                  60

Pro Val Leu Pro Leu Glu Leu Thr Val Thr Cys Asn Phe Ile Ile Leu
65                  70                  75                  80

Arg Ala Ser Leu Ala Gln Gly Phe Thr Glu Asp Gln Ala Gln Asp Ile
                85                  90                  95

Gln Arg Ser Leu Glu Arg Val Leu Glu Thr Gln Glu Gln Gln Gly Pro
            100                 105                 110

Arg Leu Glu Gln Gly Leu Arg Glu Leu Trp Asp Ser Val Leu Arg Ala
        115                 120                 125

Ser Cys Leu Leu Pro Glu Leu Leu Ser Ala Leu His Arg Leu Val Gly
    130                 135                 140

Leu Gln Ala Ala Leu Trp Leu Ser Ala Asp Arg Leu Gly Asp Leu Ala
145                 150                 155                 160

Leu Leu Leu Glu Thr Leu Asn Gly Ser Gln Ser Gly Ala Ser Lys Asp
                165                 170                 175

Leu Leu Leu Leu Leu Lys Thr Trp Ser Pro Ala Glu Glu Leu Asp
            180                 185                 190

Ala Pro Leu Thr Leu Gln Asp Ala Gln Gly Leu Lys Asp Val Leu Leu
        195                 200                 205

Thr Ala Phe Ala Tyr Arg Gln Gly Leu Gln Glu Leu Ile Thr Gly Asn
    210                 215                 220

Pro Asp Lys Ala Leu Ser Ser Leu His Glu Ala Ala Ser Gly Leu Cys
225                 230                 235                 240

Pro Arg Pro Val Leu Val Gln Val Tyr Thr Ala Leu Gly Ser Cys His
                245                 250                 255

Arg Lys Met Gly Asn Pro Gln Arg Ala Leu Leu Tyr Leu Val Ala Ala
            260                 265                 270

Leu Lys Glu Gly Ser Ala Trp Gly Pro Pro Leu Leu Glu Ala Ser Arg
        275                 280                 285
```

```
Leu Tyr Gln Gln Leu Gly Asp Thr Thr Ala Glu Leu Glu Ser Leu Glu
    290                 295                 300

Leu Leu Val Glu Ala Leu Asn Val Pro Cys Ser Ser Lys Ala Pro Gln
305                 310                 315                 320

Phe Leu Ile Glu Val Glu Leu Leu Pro Pro Asp Leu Ala Ser
                325                 330                 335

Pro Leu His Cys Gly Thr Gln Ser Gln Thr Lys His Ile Leu Ala Ser
            340                 345                 350

Arg Cys Leu Gln Thr Gly Arg Ala Gly Asp Ala Ala Glu His Tyr Leu
            355                 360                 365

Asp Leu Ala Leu Leu Leu Asp Ser Ser Glu Pro Arg Phe Ser Pro
    370                 375                 380

Pro Ser Pro Pro Gly Pro Cys Met Pro Glu Val Phe Leu Glu Ala
385                 390                 395                 400

Ala Val Ala Leu Ile Gln Ala Gly Arg Ala Gln Asp Ala Leu Thr Leu
                405                 410                 415

Cys Glu Glu Leu Leu Ser Arg Thr Ser Ser Leu Leu Pro Lys Met Ser
                420                 425                 430

Arg Leu Trp Glu Asp Ala Arg Lys Gly Thr Lys Glu Leu Pro Tyr Cys
    435                 440                 445

Pro Leu Trp Val Ser Ala Thr His Leu Leu Gln Gly Gln Ala Trp Val
    450                 455                 460

Gln Leu Gly Ala Gln Lys Val Ala Ile Ser Glu Phe Ser Arg Cys Leu
465                 470                 475                 480

Glu Leu Leu Phe Arg Ala Thr Pro Glu Glu Lys Glu Gln Gly Ala Ala
                485                 490                 495

Phe Asn Cys Glu Gln Gly Cys Lys Ser Asp Ala Ala Leu Gln Gln Leu
            500                 505                 510

Arg Ala Ala Ala Leu Ile Ser Arg Gly Leu Glu Trp Val Ala Ser Gly
            515                 520                 525

Gln Asp Thr Lys Ala Leu Gln Asp Phe Leu Leu Ser Val Gln Met Cys
    530                 535                 540

Pro Gly Asn Arg Asp Thr Tyr Phe His Leu Leu Gln Thr Leu Lys Arg
545                 550                 555                 560

Leu Asp Arg Arg Asp Glu Ala Thr Ala Leu Trp Trp Arg Leu Glu Ala
            565                 570                 575

Gln Thr Lys Gly Ser His Glu Asp Ala Leu Trp Ser Leu Pro Leu Tyr
            580                 585                 590

Leu Glu Ser Tyr Leu Ser Trp Ile Arg Pro Ser Asp Arg Asp Ala Phe
    595                 600                 605

Leu Glu Glu Phe Arg Thr Ser Leu Pro Lys Ser Cys Asp Leu
    610                 615                 620

<210> SEQ ID NO 14
<211> LENGTH: 1833
<212> TYPE: PRT
<213> ORGANISM: homo sapiens
<220> FEATURE:
<221> NAME/KEY: MISC_FEATURE
<223> OTHER INFORMATION: amino acid sequence of the SLX4 protein
      (corresponding to NP_115820.2)

<400> SEQUENCE: 14

Met Lys Leu Ser Val Asn Glu Ala Gln Leu Gly Phe Tyr Leu Gly Ser
1               5                   10                  15
```

```
Leu Ser His Leu Ser Ala Cys Pro Gly Ile Asp Pro Arg Ser Glu
        20                  25                  30

Asp Gln Pro Glu Ser Leu Lys Thr Gly Gln Met Met Asp Glu Ser Asp
    35                  40                  45

Glu Asp Phe Lys Glu Leu Cys Ala Ser Phe Phe Gln Arg Val Lys Lys
50                  55                  60

His Gly Ile Lys Glu Val Ser Gly Glu Arg Lys Thr Gln Lys Ala Ala
65                  70                  75                  80

Ser Asn Gly Thr Gln Ile Arg Ser Lys Leu Lys Arg Thr Lys Gln Thr
                85                  90                  95

Ala Thr Lys Thr Lys Thr Leu Gln Gly Pro Ala Glu Lys Lys Pro Pro
            100                 105                 110

Ser Gly Ser Gln Ala Pro Arg Thr Lys Lys Gln Arg Val Thr Lys Trp
        115                 120                 125

Gln Ala Ser Glu Pro Ala His Ser Val Asn Gly Glu Gly Gly Val Leu
    130                 135                 140

Ala Ser Ala Pro Asp Pro Pro Val Leu Arg Glu Thr Ala Gln Asn Thr
145                 150                 155                 160

Gln Thr Gly Asn Gln Gln Glu Pro Ser Pro Asn Leu Ser Arg Glu Lys
                165                 170                 175

Thr Arg Glu Asn Val Pro Asn Ser Asp Ser Gln Pro Pro Pro Ser Cys
            180                 185                 190

Leu Thr Thr Ala Val Pro Ser Pro Ser Lys Pro Arg Thr Ala Gln Leu
        195                 200                 205

Val Leu Gln Arg Met Gln Gln Phe Lys Arg Ala Asp Pro Glu Arg Leu
    210                 215                 220

Arg His Ala Ser Glu Glu Cys Ser Leu Glu Ala Ala Arg Glu Glu Asn
225                 230                 235                 240

Val Pro Lys Asp Pro Gln Glu Met Met Ala Gly Asn Val Tyr Gly
                245                 250                 255

Leu Gly Pro Pro Ala Pro Glu Ser Asp Ala Ala Val Ala Leu Thr Leu
            260                 265                 270

Gln Gln Glu Phe Ala Arg Val Gly Ala Ser Ala His Asp Asp Ser Leu
        275                 280                 285

Glu Glu Lys Gly Leu Phe Phe Cys Gln Ile Cys Gln Lys Asn Leu Ser
    290                 295                 300

Ala Met Asn Val Thr Arg Arg Glu Gln His Val Asn Arg Cys Leu Asp
305                 310                 315                 320

Glu Ala Glu Lys Thr Leu Arg Pro Ser Val Pro Gln Ile Pro Glu Cys
                325                 330                 335

Pro Ile Cys Gly Lys Pro Phe Leu Thr Leu Lys Ser Arg Thr Ser His
            340                 345                 350

Leu Lys Gln Cys Ala Val Lys Met Glu Val Gly Pro Gln Leu Leu Leu
        355                 360                 365

Gln Ala Val Arg Leu Gln Thr Ala Gln Pro Glu Gly Ser Ser Ser Pro
    370                 375                 380

Pro Met Phe Ser Phe Ser Asp His Ser Arg Gly Leu Lys Arg Arg Gly
385                 390                 395                 400

Pro Thr Ser Lys Lys Glu Pro Arg Lys Arg Lys Val Asp Glu Ala
                405                 410                 415

Pro Ser Glu Asp Leu Leu Val Ala Met Ala Leu Ser Arg Ser Glu Met
            420                 425                 430

Glu Pro Gly Ala Ala Val Pro Ala Leu Arg Leu Glu Ser Ala Phe Ser
```

-continued

```
            435                 440                 445
Glu Arg Ile Arg Pro Glu Ala Glu Asn Lys Ser Arg Lys Lys Lys Pro
450                 455                 460

Pro Val Ser Pro Pro Leu Leu Leu Val Gln Asp Ser Glu Thr Thr Gly
465                 470                 475                 480

Arg Gln Ile Glu Asp Arg Val Ala Leu Leu Ser Glu Glu Val Glu
                485                 490                 495

Leu Ser Ser Thr Pro Pro Leu Pro Ala Ser Arg Ile Leu Lys Glu Gly
                500                 505                 510

Trp Glu Arg Ala Gly Gln Cys Pro Pro Pro Glu Arg Lys Gln Ser
                515                 520                 525

Phe Leu Trp Glu Gly Ser Ala Leu Thr Gly Ala Trp Ala Met Glu Asp
530                 535                 540

Phe Tyr Thr Ala Arg Leu Val Pro Pro Leu Val Pro Gln Arg Pro Ala
545                 550                 555                 560

Gln Gly Leu Met Gln Glu Pro Val Pro Pro Leu Val Pro Pro Glu His
                565                 570                 575

Ser Glu Leu Ser Glu Arg Arg Ser Pro Ala Leu His Gly Thr Pro Thr
                580                 585                 590

Ala Gly Cys Gly Ser Arg Gly Pro Ser Pro Ser Ala Ser Gln Arg Glu
                595                 600                 605

His Gln Ala Leu Gln Asp Leu Val Asp Leu Ala Arg Glu Gly Leu Ser
610                 615                 620

Ala Ser Pro Trp Pro Gly Ser Gly Gly Leu Ala Gly Ser Glu Gly Thr
625                 630                 635                 640

Ala Gly Leu Asp Val Val Pro Gly Gly Leu Pro Leu Thr Gly Phe Val
                645                 650                 655

Val Pro Ser Gln Asp Lys His Pro Asp Arg Gly Gly Arg Thr Leu Leu
                660                 665                 670

Ser Leu Gly Leu Leu Val Ala Asp Phe Gly Ala Met Val Asn Asn Pro
                675                 680                 685

His Leu Ser Asp Val Gln Phe Gln Thr Asp Ser Gly Glu Val Leu Tyr
690                 695                 700

Ala His Lys Phe Val Leu Tyr Ala Arg Cys Pro Leu Leu Ile Gln Tyr
705                 710                 715                 720

Val Asn Asn Glu Gly Phe Ser Ala Val Glu Asp Gly Val Leu Thr Gln
                725                 730                 735

Arg Val Leu Leu Gly Asp Val Ser Thr Glu Ala Ala Arg Thr Phe Leu
                740                 745                 750

His Tyr Leu Tyr Thr Ala Asp Thr Gly Leu Pro Pro Gly Leu Ser Ser
                755                 760                 765

Glu Leu Ser Ser Leu Ala His Arg Phe Gly Val Ser Glu Leu Val His
770                 775                 780

Leu Cys Glu Gln Val Pro Ile Ala Thr Asp Ser Glu Gly Lys Pro Trp
785                 790                 795                 800

Glu Glu Lys Glu Ala Glu Asn Cys Glu Ser Arg Ala Glu Asn Phe Gln
                805                 810                 815

Glu Leu Leu Arg Ser Met Trp Ala Asp Glu Glu Glu Ala Glu Thr
                820                 825                 830

Leu Leu Lys Ser Lys Asp His Glu Glu Asp Gln Glu Asn Val Asn Glu
                835                 840                 845

Ala Glu Met Glu Glu Ile Tyr Glu Phe Ala Ala Thr Gln Arg Lys Leu
850                 855                 860
```

-continued

```
Leu Gln Glu Glu Arg Ala Ala Gly Ala Gly Glu Asp Ala Asp Trp Leu
865                 870                 875                 880

Glu Gly Gly Ser Pro Val Ser Gly Gln Leu Leu Ala Gly Val Gln Val
            885                 890                 895

Gln Lys Gln Trp Asp Lys Val Glu Met Glu Pro Leu Glu Pro Gly
        900                 905                 910

Arg Asp Glu Ala Ala Thr Thr Trp Glu Lys Met Gly Gln Cys Ala Leu
        915                 920                 925

Pro Pro Pro Gln Gly Gln His Ser Gly Ala Arg Gly Ala Glu Ala Pro
        930                 935                 940

Glu Gln Glu Ala Pro Glu Ala Leu Gly His Ser Ser Cys Ser Ser
945                 950                 955                 960

Pro Ser Arg Asp Cys Gln Ala Glu Arg Lys Glu Gly Ser Leu Pro His
            965                 970                 975

Ser Asp Asp Ala Gly Asp Tyr Glu Gln Leu Phe Ser Ser Thr Gln Gly
            980                 985                 990

Glu Ile Ser Glu Pro Ser Gln Ile Thr Ser Glu Pro Glu Glu Gln Ser
            995                 1000                1005

Gly Ala Val Arg Glu Arg Gly Leu Glu Val Ser His Arg Leu Ala
        1010                1015                1020

Pro Trp Gln Ala Ser Pro Pro His Pro Cys Arg Phe Leu Leu Gly
        1025                1030                1035

Pro Pro Gln Gly Gly Ser Pro Arg Gly Ser His His Thr Ser Gly
        1040                1045                1050

Ser Ser Leu Ser Thr Pro Arg Ser Arg Gly Gly Thr Ser Gln Val
        1055                1060                1065

Gly Ser Pro Thr Leu Leu Ser Pro Ala Val Pro Ser Lys Gln Lys
        1070                1075                1080

Arg Asp Arg Ser Ile Leu Thr Leu Ser Lys Glu Pro Gly His Gln
        1085                1090                1095

Lys Gly Lys Glu Arg Arg Ser Val Leu Glu Cys Arg Asn Lys Gly
        1100                1105                1110

Val Leu Met Phe Pro Glu Lys Ser Pro Ser Ile Asp Leu Thr Gln
        1115                1120                1125

Ser Asn Pro Asp His Ser Ser Arg Ser Gln Lys Ser Ser Ser
        1130                1135                1140

Lys Leu Asn Glu Glu Asp Glu Val Ile Leu Leu Leu Asp Ser Asp
        1145                1150                1155

Glu Glu Leu Glu Leu Glu Gln Thr Lys Met Lys Ser Ile Ser Ser
        1160                1165                1170

Asp Pro Leu Glu Glu Lys Lys Ala Leu Glu Ile Ser Pro Arg Ser
        1175                1180                1185

Cys Glu Leu Phe Ser Ile Ile Asp Val Asp Ala Asp Gln Glu Pro
        1190                1195                1200

Ser Gln Ser Pro Pro Arg Ser Glu Ala Val Leu Gln Gln Glu Asp
        1205                1210                1215

Glu Gly Ala Leu Pro Glu Asn Arg Gly Ser Leu Gly Arg Arg Gly
        1220                1225                1230

Ala Pro Trp Leu Phe Cys Asp Arg Glu Ser Ser Pro Ser Glu Ala
        1235                1240                1245

Ser Thr Thr Asp Thr Ser Trp Leu Val Pro Ala Thr Pro Leu Ala
        1250                1255                1260
```

```
Ser Arg Ser Arg Asp Cys Ser Ser Gln Thr Gln Ile Ser Ser Leu
    1265                1270                1275

Arg Ser Gly Leu Ala Val Gln Ala Val Thr Gln His Thr Pro Arg
    1280                1285                1290

Ala Ser Val Gly Asn Arg Glu Gly Asn Glu Val Ala Gln Lys Phe
    1295                1300                1305

Ser Val Ile Arg Pro Gln Thr Pro Pro Gln Thr Pro Ser Ser
    1310                1315                1320

Cys Leu Thr Pro Val Ser Pro Gly Thr Ser Asp Gly Arg Arg Gln
    1325                1330                1335

Gly His Arg Ser Pro Ser Arg Pro His Pro Gly Gly His Pro His
    1340                1345                1350

Ser Ser Pro Leu Ala Pro His Pro Ile Ser Gly Asp Arg Ala His
    1355                1360                1365

Phe Ser Arg Arg Phe Leu Lys His Ser Pro Pro Gly Pro Ser Phe
    1370                1375                1380

Leu Asn Gln Thr Pro Ala Gly Glu Val Val Glu Val Gly Asp Ser
    1385                1390                1395

Asp Asp Glu Gln Glu Val Ala Ser His Gln Ala Asn Arg Ser Pro
    1400                1405                1410

Pro Leu Asp Ser Asp Pro Pro Ile Pro Ile Asp Asp Cys Cys Trp
    1415                1420                1425

His Met Glu Pro Leu Ser Pro Ile Pro Ile Asp His Trp Asn Leu
    1430                1435                1440

Glu Arg Thr Gly Pro Leu Ser Thr Ser Ser Pro Ser Arg Arg Met
    1445                1450                1455

Asn Glu Ala Ala Asp Ser Arg Asp Cys Arg Ser Pro Gly Leu Leu
    1460                1465                1470

Asp Thr Thr Pro Ile Arg Gly Ser Cys Thr Thr Gln Arg Lys Leu
    1475                1480                1485

Gln Glu Lys Ser Ser Gly Ala Gly Ser Leu Gly Asn Ser Arg Pro
    1490                1495                1500

Ser Phe Leu Asn Ser Ala Leu Trp Asp Val Trp Asp Gly Glu Glu
    1505                1510                1515

Gln Arg Pro Pro Glu Thr Pro Pro Ala Gln Met Pro Ser Ala
    1520                1525                1530

Gly Gly Ala Gln Lys Pro Glu Gly Leu Glu Thr Pro Lys Gly Ala
    1535                1540                1545

Asn Arg Lys Lys Asn Leu Pro Pro Lys Val Pro Ile Thr Pro Met
    1550                1555                1560

Pro Gln Tyr Ser Ile Met Glu Thr Pro Val Leu Lys Lys Glu Leu
    1565                1570                1575

Asp Arg Phe Gly Val Arg Pro Leu Pro Lys Arg Gln Met Val Leu
    1580                1585                1590

Lys Leu Lys Glu Ile Phe Gln Tyr Thr His Gln Thr Leu Asp Ser
    1595                1600                1605

Asp Ser Glu Asp Glu Ser Gln Ser Ser Gln Pro Leu Leu Gln Ala
    1610                1615                1620

Pro His Cys Gln Thr Leu Ala Ser Gln Thr Tyr Lys Pro Ser Arg
    1625                1630                1635

Ala Gly Val His Ala Gln Gln Glu Ala Thr Thr Gly Pro Gly Ala
    1640                1645                1650

His Arg Pro Lys Gly Pro Ala Lys Thr Lys Gly Pro Arg His Gln
```

```
                  1655                1660                1665

Arg Lys His His Glu Ser Ile Thr Pro Pro Ser Arg Ser Pro Thr
    1670                1675                1680

Lys Glu Ala Pro Pro Gly Leu Asn Asp Asp Ala Gln Ile Pro Ala
    1685                1690                1695

Ser Gln Glu Ser Val Ala Thr Ser Val Asp Gly Ser Asp Ser Ser
    1700                1705                1710

Leu Ser Ser Gln Ser Ser Ser Cys Glu Phe Gly Ala Ala Phe
    1715                1720                1725

Glu Ser Ala Gly Glu Glu Glu Gly Glu Gly Val Ser Ala Ser
    1730                1735                1740

Gln Ala Ala Val Gln Ala Ala Asp Thr Asp Glu Ala Leu Arg Cys
    1745                1750                1755

Tyr Ile Arg Ser Lys Pro Ala Leu Tyr Gln Lys Val Leu Leu Tyr
    1760                1765                1770

Gln Pro Phe Glu Leu Arg Glu Leu Gln Ala Glu Leu Arg Gln Asn
    1775                1780                1785

Gly Leu Arg Val Ser Ser Arg Arg Leu Leu Asp Phe Asp Thr His
    1790                1795                1800

Cys Ile Thr Phe Thr Thr Ala Ala Thr Arg Arg Glu Lys Leu Gln
    1805                1810                1815

Gly Arg Arg Arg Gln Pro Arg Gly Lys Lys Lys Val Glu Arg Asn
    1820                1825                1830

<210> SEQ ID NO 15
<211> LENGTH: 1056
<212> TYPE: PRT
<213> ORGANISM: homo sapiens
<220> FEATURE:
<221> NAME/KEY: MISC_FEATURE
<223> OTHER INFORMATION: amino acid sequence of the kinesin-related
      motor protein Eg5 (corresponding to NP_004514.2) (Note: the
      official symbol of the corresponding coding gene is KIF11)

<400> SEQUENCE: 15

Met Ala Ser Gln Pro Asn Ser Ser Ala Lys Lys Lys Glu Glu Lys Gly
1               5                   10                  15

Lys Asn Ile Gln Val Val Val Arg Cys Arg Pro Phe Asn Leu Ala Glu
                20                  25                  30

Arg Lys Ala Ser Ala His Ser Ile Val Glu Cys Asp Pro Val Arg Lys
            35                  40                  45

Glu Val Ser Val Arg Thr Gly Gly Leu Ala Asp Lys Ser Ser Arg Lys
        50                  55                  60

Thr Tyr Thr Phe Asp Met Val Phe Gly Ala Ser Thr Lys Gln Ile Asp
65                  70                  75                  80

Val Tyr Arg Ser Val Val Cys Pro Ile Leu Asp Glu Val Ile Met Gly
                85                  90                  95

Tyr Asn Cys Thr Ile Phe Ala Tyr Gly Gln Thr Gly Thr Gly Lys Thr
            100                 105                 110

Phe Thr Met Glu Gly Glu Arg Ser Pro Asn Glu Glu Tyr Thr Trp Glu
        115                 120                 125

Glu Asp Pro Leu Ala Gly Ile Ile Pro Arg Thr Leu His Gln Ile Phe
    130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
```

```
                165                 170                 175
Asp Val Ser Glu Arg Leu Gln Met Phe Asp Pro Arg Asn Lys Arg
                180                 185                 190
Gly Val Ile Ile Lys Gly Leu Glu Glu Ile Thr Val His Asn Lys Asp
                195                 200                 205
Glu Val Tyr Gln Ile Leu Glu Lys Gly Ala Ala Lys Arg Thr Thr Ala
                210                 215                 220
Ala Thr Leu Met Asn Ala Tyr Ser Ser Arg Ser His Ser Val Phe Ser
225                 230                 235                 240
Val Thr Ile His Met Lys Glu Thr Thr Ile Asp Gly Glu Glu Leu Val
                245                 250                 255
Lys Ile Gly Lys Leu Asn Leu Val Asp Leu Ala Gly Ser Glu Asn Ile
                260                 265                 270
Gly Arg Ser Gly Ala Val Asp Lys Arg Ala Arg Glu Ala Gly Asn Ile
                275                 280                 285
Asn Gln Ser Leu Leu Thr Leu Gly Arg Val Ile Thr Ala Leu Val Glu
                290                 295                 300
Arg Thr Pro His Val Pro Tyr Arg Glu Ser Lys Leu Thr Arg Ile Leu
305                 310                 315                 320
Gln Asp Ser Leu Gly Gly Arg Thr Arg Thr Ser Ile Ile Ala Thr Ile
                325                 330                 335
Ser Pro Ala Ser Leu Asn Leu Glu Glu Thr Leu Ser Thr Leu Glu Tyr
                340                 345                 350
Ala His Arg Ala Lys Asn Ile Leu Asn Lys Pro Glu Val Asn Gln Lys
                355                 360                 365
Leu Thr Lys Lys Ala Leu Ile Lys Glu Tyr Thr Glu Glu Ile Glu Arg
370                 375                 380
Leu Lys Arg Asp Leu Ala Ala Ala Arg Glu Lys Asn Gly Val Tyr Ile
385                 390                 395                 400
Ser Glu Glu Asn Phe Arg Val Met Ser Gly Lys Leu Thr Val Gln Glu
                405                 410                 415
Glu Gln Ile Val Glu Leu Ile Glu Lys Ile Gly Ala Val Glu Glu Glu
                420                 425                 430
Leu Asn Arg Val Thr Glu Leu Phe Met Asp Asn Lys Asn Glu Leu Asp
                435                 440                 445
Gln Cys Lys Ser Asp Leu Gln Asn Lys Thr Gln Glu Leu Glu Thr Thr
450                 455                 460
Gln Lys His Leu Gln Glu Thr Lys Leu Gln Leu Val Lys Glu Glu Tyr
465                 470                 475                 480
Ile Thr Ser Ala Leu Glu Ser Thr Glu Glu Lys Leu His Asp Ala Ala
                485                 490                 495
Ser Lys Leu Leu Asn Thr Val Glu Glu Thr Thr Lys Asp Val Ser Gly
                500                 505                 510
Leu His Ser Lys Leu Asp Arg Lys Lys Ala Val Asp Gln His Asn Ala
                515                 520                 525
Glu Ala Gln Asp Ile Phe Gly Lys Asn Leu Asn Ser Leu Phe Asn Asn
                530                 535                 540
Met Glu Glu Leu Ile Lys Asp Gly Ser Ser Lys Gln Lys Ala Met Leu
545                 550                 555                 560
Glu Val His Lys Thr Leu Phe Gly Asn Leu Leu Ser Ser Ser Val Ser
                565                 570                 575
Ala Leu Asp Thr Ile Thr Thr Val Ala Leu Gly Ser Leu Thr Ser Ile
                580                 585                 590
```

-continued

```
Pro Glu Asn Val Ser Thr His Val Ser Gln Ile Phe Asn Met Ile Leu
    595                 600                 605
Lys Glu Gln Ser Leu Ala Ala Glu Ser Lys Thr Val Leu Gln Glu Leu
610                 615                 620
Ile Asn Val Leu Lys Thr Asp Leu Leu Ser Ser Leu Glu Met Ile Leu
625                 630                 635                 640
Ser Pro Thr Val Ser Ile Leu Lys Ile Asn Ser Gln Leu Lys His
                645                 650                 655
Ile Phe Lys Thr Ser Leu Thr Val Ala Asp Lys Ile Glu Asp Gln Lys
                660                 665                 670
Lys Glu Leu Asp Gly Phe Leu Ser Ile Leu Cys Asn Asn Leu His Glu
                675                 680                 685
Leu Gln Glu Asn Thr Ile Cys Ser Leu Val Glu Ser Gln Lys Gln Cys
                690                 695                 700
Gly Asn Leu Thr Glu Asp Leu Lys Thr Ile Lys Gln Thr His Ser Gln
705                 710                 715                 720
Glu Leu Cys Lys Leu Met Asn Leu Trp Thr Glu Arg Phe Cys Ala Leu
                725                 730                 735
Glu Glu Lys Cys Glu Asn Ile Gln Lys Pro Leu Ser Ser Val Gln Glu
                740                 745                 750
Asn Ile Gln Gln Lys Ser Lys Asp Ile Val Asn Lys Met Thr Phe His
                755                 760                 765
Ser Gln Lys Phe Cys Ala Asp Ser Asp Gly Phe Ser Gln Glu Leu Arg
                770                 775                 780
Asn Phe Asn Gln Glu Gly Thr Lys Leu Val Glu Ser Val Lys His
785                 790                 795                 800
Ser Asp Lys Leu Asn Gly Asn Leu Glu Lys Ile Ser Gln Glu Thr Glu
                805                 810                 815
Gln Arg Cys Glu Ser Leu Asn Thr Arg Thr Val Tyr Phe Ser Glu Gln
                820                 825                 830
Trp Val Ser Ser Leu Asn Glu Arg Glu Gln Glu Leu His Asn Leu Leu
                835                 840                 845
Glu Val Val Ser Gln Cys Cys Glu Ala Ser Ser Asp Ile Thr Glu
                850                 855                 860
Lys Ser Asp Gly Arg Lys Ala Ala His Glu Lys Gln His Asn Ile Phe
865                 870                 875                 880
Leu Asp Gln Met Thr Ile Asp Glu Asp Lys Leu Ile Ala Gln Asn Leu
                885                 890                 895
Glu Leu Asn Glu Thr Ile Lys Ile Gly Leu Thr Lys Leu Asn Cys Phe
                900                 905                 910
Leu Glu Gln Asp Leu Lys Leu Asp Ile Pro Thr Gly Thr Thr Pro Gln
                915                 920                 925
Arg Lys Ser Tyr Leu Tyr Pro Ser Thr Leu Val Arg Thr Glu Pro Arg
930                 935                 940
Glu His Leu Leu Asp Gln Leu Lys Arg Lys Gln Pro Glu Leu Leu Met
945                 950                 955                 960
Met Leu Asn Cys Ser Glu Asn Asn Lys Glu Glu Thr Ile Pro Asp Val
                965                 970                 975
Asp Val Glu Glu Ala Val Leu Gly Gln Tyr Thr Glu Glu Pro Leu Ser
                980                 985                 990
Gln Glu Pro Ser Val Asp Ala Gly  Val Asp Cys Ser Ser  Ile Gly Gly
                995                 1000                1005
```

```
Val Pro Phe Phe Gln His Lys Lys Ser His Gly Lys Asp Lys Glu
    1010                1015                1020

Asn Arg Gly Ile Asn Thr Leu Glu Arg Ser Lys Val Glu Glu Thr
    1025                1030                1035

Thr Glu His Leu Val Thr Lys Ser Arg Leu Pro Leu Arg Ala Gln
    1040                1045                1050

Ile Asn Leu
    1055

<210> SEQ ID NO 16
<211> LENGTH: 205
<212> TYPE: PRT
<213> ORGANISM: homo sapiens
<220> FEATURE:
<221> NAME/KEY: MISC_FEATURE
<223> OTHER INFORMATION: amino acid sequence of the MAD2A protein
      (corresponding to NP_002349.1). (Note: the official symbol of the
      corresponding coding gene is MAD2L1)

<400> SEQUENCE: 16

Met Ala Leu Gln Leu Ser Arg Glu Gln Gly Ile Thr Leu Arg Gly Ser
1               5                   10                  15

Ala Glu Ile Val Ala Glu Phe Phe Ser Phe Gly Ile Asn Ser Ile Leu
            20                  25                  30

Tyr Gln Arg Gly Ile Tyr Pro Ser Glu Thr Phe Thr Arg Val Gln Lys
        35                  40                  45

Tyr Gly Leu Thr Leu Leu Val Thr Thr Asp Leu Glu Leu Ile Lys Tyr
    50                  55                  60

Leu Asn Asn Val Val Glu Gln Leu Lys Asp Trp Leu Tyr Lys Cys Ser
65                  70                  75                  80

Val Gln Lys Leu Val Val Val Ile Ser Asn Ile Glu Ser Gly Glu Val
                85                  90                  95

Leu Glu Arg Trp Gln Phe Asp Ile Glu Cys Asp Lys Thr Ala Lys Asp
            100                 105                 110

Asp Ser Ala Pro Arg Glu Lys Ser Gln Lys Ala Ile Gln Asp Glu Ile
        115                 120                 125

Arg Ser Val Ile Arg Gln Ile Thr Ala Thr Val Thr Phe Leu Pro Leu
    130                 135                 140

Leu Glu Val Ser Cys Ser Phe Asp Leu Leu Ile Tyr Thr Asp Lys Asp
145                 150                 155                 160

Leu Val Val Pro Glu Lys Trp Glu Glu Ser Gly Pro Gln Phe Ile Thr
                165                 170                 175

Asn Ser Glu Glu Val Arg Leu Arg Ser Phe Thr Thr Thr Ile His Lys
            180                 185                 190

Val Asn Ser Met Val Ala Tyr Lys Ile Pro Val Asn Asp
        195                 200                 205

<210> SEQ ID NO 17
<211> LENGTH: 542
<212> TYPE: PRT
<213> ORGANISM: homo sapiens
<220> FEATURE:
<221> NAME/KEY: MISC_FEATURE
<223> OTHER INFORMATION: amino acid sequence of the TRF2 (corresponding
      to NP_005643.2). (Note: the official symbol of the corresponding
      coding gene is TERF2)

<400> SEQUENCE: 17

Met Ala Ala Gly Ala Gly Thr Ala Gly Pro Ala Ser Gly Pro Gly Val
1               5                   10                  15
```

```
Val Arg Asp Pro Ala Ala Ser Gln Pro Arg Lys Arg Pro Gly Arg Glu
            20                  25                  30

Gly Gly Glu Gly Ala Arg Arg Ser Asp Thr Met Ala Gly Gly Gly
        35                  40                  45

Ser Ser Asp Gly Ser Gly Arg Ala Ala Gly Arg Arg Ala Ser Arg Ser
50                  55                  60

Ser Gly Arg Ala Arg Arg Gly Arg His Glu Pro Gly Leu Gly Gly Pro
65                  70                  75                  80

Ala Glu Arg Gly Ala Gly Glu Ala Arg Leu Glu Ala Val Asn Arg
                85                  90                  95

Trp Val Leu Lys Phe Tyr Phe His Glu Ala Leu Arg Ala Phe Arg Gly
                100                 105                 110

Ser Arg Tyr Gly Asp Phe Arg Gln Ile Arg Asp Ile Met Gln Ala Leu
            115                 120                 125

Leu Val Arg Pro Leu Gly Lys Glu His Thr Val Ser Arg Leu Leu Arg
    130                 135                 140

Val Met Gln Cys Leu Ser Arg Ile Glu Glu Gly Glu Asn Leu Asp Cys
145                 150                 155                 160

Ser Phe Asp Met Glu Ala Glu Leu Thr Pro Leu Glu Ser Ala Ile Asn
                165                 170                 175

Val Leu Glu Met Ile Lys Thr Glu Phe Thr Leu Thr Glu Ala Val Val
                180                 185                 190

Glu Ser Ser Arg Lys Leu Val Lys Glu Ala Ala Val Ile Ile Cys Ile
    195                 200                 205

Lys Asn Lys Glu Phe Glu Lys Ala Ser Lys Ile Leu Lys Lys His Met
    210                 215                 220

Ser Lys Asp Pro Thr Thr Gln Lys Leu Arg Asn Asp Leu Leu Asn Ile
225                 230                 235                 240

Ile Arg Glu Lys Asn Leu Ala His Pro Val Ile Gln Asn Phe Ser Tyr
                245                 250                 255

Glu Thr Phe Gln Gln Lys Met Leu Arg Phe Leu Glu Ser His Leu Asp
                260                 265                 270

Asp Ala Glu Pro Tyr Leu Leu Thr Met Ala Lys Ala Leu Lys Ser
            275                 280                 285

Glu Ser Ala Ala Ser Ser Thr Gly Lys Glu Asp Lys Gln Pro Ala Pro
    290                 295                 300

Gly Pro Val Glu Lys Pro Pro Arg Glu Pro Ala Arg Gln Leu Arg Asn
305                 310                 315                 320

Pro Pro Thr Thr Ile Gly Met Met Thr Leu Lys Ala Ala Phe Lys Thr
                325                 330                 335

Leu Ser Gly Ala Gln Asp Ser Glu Ala Ala Phe Ala Lys Leu Asp Gln
            340                 345                 350

Lys Asp Leu Val Leu Pro Thr Gln Ala Leu Pro Ala Ser Pro Ala Leu
    355                 360                 365

Lys Asn Lys Arg Pro Arg Lys Asp Glu Asn Glu Ser Ser Ala Pro Ala
    370                 375                 380

Asp Gly Glu Gly Gly Ser Glu Leu Gln Pro Lys Asn Lys Arg Met Thr
385                 390                 395                 400

Ile Ser Arg Leu Val Leu Glu Glu Asp Ser Gln Ser Thr Glu Pro Ser
                405                 410                 415

Ala Gly Leu Asn Ser Ser Gln Glu Ala Ala Ser Ala Pro Pro Ser Lys
            420                 425                 430
```

```
Pro Thr Val Leu Asn Gln Pro Leu Pro Gly Glu Lys Asn Pro Lys Val
        435                 440                 445
Pro Lys Gly Lys Trp Asn Ser Ser Asn Gly Val Glu Glu Lys Glu Thr
    450                 455                 460
Trp Val Glu Glu Asp Glu Leu Phe Gln Val Gln Ala Ala Pro Asp Glu
465                 470                 475                 480
Asp Ser Thr Thr Asn Ile Thr Lys Lys Gln Lys Trp Thr Val Glu Glu
                485                 490                 495
Ser Glu Trp Val Lys Ala Gly Val Gln Lys Tyr Gly Glu Gly Asn Trp
            500                 505                 510
Ala Ala Ile Ser Lys Asn Tyr Pro Phe Val Asn Arg Thr Ala Val Met
        515                 520                 525
Ile Lys Asp Arg Trp Arg Thr Met Lys Arg Leu Gly Met Asn
    530                 535                 540
```

EXPRESSION OF ISOFORM 202 OF ERCC1 FOR PREDICTING RESPONSE TO CANCER CHEMOTHERAPY

Sequence Listing contained in file D27420362944ST25.txt having a file size of 80.0 KB is hereby incorporated-by-reference.

TECHNICAL FIELD OF THE INVENTION

The present invention is directed to the detection of the Excision Repair Cross-Complementation group 1 (ERCC1) enzyme, and more specifically of the isoform 202 of this enzyme, and its use in the detection of the susceptibility of a tumor cell to chemotherapy, especially to platinating agents-based cancer chemotherapy. The invention also concerns a kit for detection, carrying out the method.

BACKGROUND OF THE INVENTION

Lung cancer is a leading cause of cancer deaths in most industrialized countries (Jemal A, Murray T, Ward E, et al. Cancer statistics, 2005). Despite complete tumor resection in patients with stage I-III non-small-cell lung cancer, distant metastases develop in 50-70 percent of patients.

Adjuvant chemotherapy has been tested to improve survival in patients with completely resected non-small-cell lung cancer. The recently reported International Adjuvant Lung Cancer Trial (IALT) with 1,867 patients, was designed to assess the potential benefit of adjuvant cisplatin-based chemotherapy after complete resection of non-small cell lung cancer. The IALT demonstrated a 4.1 percent absolute benefit in 5-year overall survival in non-small-cell lung cancer patients treated with adjuvant cisplatin-based chemotherapy (the International Adjuvant Lung Cancer Trial Collaborative Group. Cisplatin-based adjuvant chemotherapy in patients with completely resected non-small-cell lung cancer. *N Engl J Med* 2004). Several other randomized studies have confirmed the benefit of postoperative platinum-based therapy in non-small-cell lung cancer (Gurubhagavatula S, Lynch T J. *Semin Respir Crit. Care Med* 2005). However, adjuvant chemotherapy only slightly prolongs survival, with a 5-year overall survival improvement ranging from 4 to 15 percent, and gives rise to significant adverse effects (Winton T, et al. *N Engl J Med* 2005). The identification and quantification of predictive factors for resistance or sensitivity to adjuvant cisplatin-based chemotherapy were therefore needed.

Among potential predictive factors are those involved in cisplatin-resistance such as DNA repair mechanisms. Cisplatin induces cytotoxic effects by binding to DNA and creating platinum-DNA adducts. Some of these adducts establish covalent cross-linking between DNA strands, thereby inhibiting DNA replication. Among the DNA repair pathways, nucleotide excision repair plays a central role and has been associated with resistance to platinum-based chemotherapy (Reed E. *Cancer Treat Rev* 1998). The excision repair cross-complementation group 1 (ERCC1) enzyme plays a rate-limiting role in the nucleotide excision repair pathway which recognizes and removes cisplatin-induced DNA adducts (Zamble D B. et al. *Biochemistry* 1996). ERCC1 is also an important factor in DNA interstrand cross-link repair, as well as in recombination processes (De Silva I U. et al. *Mol Cell Biol* 2000).

For more than a decade, smaller studies have repeatedly reported an association between low ERCC1 mRNA expression levels in several solid tumors and improved clinical outcomes in patients treated with platinum-containing regimens (Dabholkar M. et al *J Clin Invest* 1994). In particular, Lord et al (Lord R V et al. *Clin Cancer Res* 2002) reported that ERCC1 mRNA expression predicts response to chemotherapy in advanced non-small-cell lung cancer. Furthermore, by using methodologies such as DNA isolation, enzymatic digestions, and DNA sequencing, two common polymorphisms of the ERCC1 gene (codon 118 C/T and C8092A) were found to be correlated with response to platinum-based chemotherapy in colorectal (Viguier J. et al. *Clin Cancer Res* 2005) and non-small-cell lung cancer (Zhou W. et al. *Clin Cancer Res* 2004). These polymorphisms are mainly associated with lower translation rates of the ERCC1 gene, resulting in low expression levels.

The invention described in the international application WO 02/061128 (published on 8 Aug. 2002) relates to prognostic methods for cisplatin-based cancer chemotherapy assessing ERCC1 expression levels. These prognostic tests consist of (i) determining a platinum-based chemotherapy by examination of the amount of ERCC1 mRNA in patient's tumor cells and (ii) comparing it to a pre-determined threshold expression level. Such quantitative gene expression studies were developed for formalin-fixed paraffin-embedded pathological samples because most tumor samples are routinely formalin-fixed paraffin-embedded to allow histological analysis and subsequent archival storage. In this method, all the patients were treated with a platinum-based chemotherapy and the ERCC1 level was assessed so as to prognose the survival probability of the treated patients. Nevertheless, (i) techniques for the isolation and analyses of mRNA from formalin-fixed paraffin-embedded tissue samples are frequently inaccurate, costly and time-consuming and (ii) the conservation of mRNA in formalin-fixed paraffin-embedded samples is eventually affected with time. For these reasons, such analyses are carried out with difficulty by the skilled person, especially in large-scale studies. Other techniques, allowing an easier, more accurate and less expensive measure of the expression of ERCC1 are thus particularly needed.

Moreover, since the study on which the international application WO 02/061128 (published on 8 Aug. 2002) was based did not compare two groups of patients according to whether or not they were treated with cisplatin, the value of ERCC1 mRNA expression as evidenced in this study is only prognostic, and not predictive of the patient response to a chemotherapy.

A biomarker has a "prognostic value" if it enables to distinguish patients with high probability of survival from those who have low probability of survival, regardless of treatment or in a population where all patients received an identical treatment.

On another hand, a biomarker as a "predictive value" for a specific treatment if it enables to distinguish patients who have a high probability of clinical benefit (in terms of survival) from those who will take no benefit from said specific treatment. A predictive value of a biomarker can therefore only be demonstrated when two study groups are compared directly (a treated group against a non-treated group).

Furthermore, other studies have investigated the relation between the expression of different markers, like ERCC1, the platinum resistance and the prognosis in advanced non small cell lung cancer. Indeed, the scientific publication of Huang P Y et al. *Chinese Journal of Cancer* 2004 aims at determining prognostic values of different markers, like ERCC1, in response of a first-line platinum-based treatment. ERCC1 has been detected by immunohistochemistry. This study indicates that no prognostic value of ERCC1 expression can be demonstrated. On another hand, the publication of Watchers F M et al. *Lung Cancer* 2005 describes a study to determine a prognostic value of different protein expression involved in DNA repair. Among them, ERCC1 expression is measured in phase III-NSCLC patients by comparing first-line "cisplatin-gemcitabine" and "epirubicin-gemcitabine" chemotherapies. The ERCC1 expression was measured by immunohistochemistry on formalin-fixed, paraffin-embedded tumor biopsies. This document concludes that these markers (including ERCC1) are not prognostic of patient survival after these chemotherapies. Those two documents conclude that ERCC1 has no prognostic value of the efficiency of chemotherapy treatment.

BRIEF SUMMARY OF THE INVENTION

These and other shortcomings of the prior art are addressed by the present invention, which provides an in vitro method for detecting the susceptibility of a tumor cell to a chemotherapy.

This invention differs from the anterior art, particularly the scientific publications of Huang P Y et al. *Chinese Journal of Cancer* 2004 and Watchers F M et al. *Lung Cancer* 2005 by the fact that the steps which have been carried out in said immunohistochemical method are different from those in these precedent documents wherein ERCC1 was not described as a predictive marker of a chemotherapy efficiency, but as a prognostic marker in patients treated by chemotherapy.

The method of the invention comprises the step of assessing the expression level of the isoform 202 of the ERCC1 protein. In a preferred embodiment of the invention, the said expression level is assessed by measuring the mRNA level of the isoform 202 of the ERCC1 protein, for example by RT-PCR or in situ hybridization. Alternatively, immunological methods aimed at measuring directly the protein level of the isoform 202 of ERCC1 (e.g., immunohistochemical or immunofluorescence assays) can be used.

Using an immunohistochemical assay, the inventors demonstrated, in a quantitative and reproducible way, that patients with ERCC1-negative tumors have a risk of death decreased by 33% (hazard ratio 0.67) when cisplatin based chemotherapy is added to surgery. On the other hand, the inventors have found that the risk of death was not decreased by the adjunction of chemotherapy among patients with ERCC1-positive tumors (hazard ratio 1.18) (Olaussen et al, NEJM, 2006). These results had been obtained with an anti-ERCC1 antibody recognizing, possibly among other isoforms, the isoform 202 of ERCC1.

It was stated in the patent application WO 02/061128 that protein expression levels could be only qualitatively monitored in formalin-fixed paraffin-embedded samples by using immunohistochemical methods. However, the present inventors have developed other quantitative and reproducible methods for assessing ERCC1 expression levels which is the subject matter of the present invention.

The analyses of the protein or mRNA level by the said methods are predictive of survival in early-stage and completely resected non-small cell lung cancer. Because immunological assays and mRNA analyses can be easily applied in every pathology laboratory, the present invention is therefore widely applicable and a useful test in clinical practice.

In a particular embodiment, the method of the invention also presents an additional advantage which is to be able to analyze formalin-fixed paraffin-embedded tumor samples, whatever the fixation techniques are.

The ERCC1 gene generates four isoforms (designated 201, 202, 203, and 204) by alternative splicing. As shown recently in Friboulet et al. (2013), using immunohistochemical analysis, the present Inventors showed that the level of biologic complexity of the ERCC1 protein had been underestimated and that the respective roles of the four ERCC1 protein isoforms had not been correctly assessed. In fact, they showed that the expression of nonfunctional ERCC1 isoforms leads to potential artifacts, with discrepant results.

More precisely, in this study, they demonstrated that only the reintroduction of the ERCC1-202 isoform rescued nucleotide excision repair activity and the capacity to repair cisplatin-induced DNA damage in established ERCC1-deficient cells. In terms of patient classification and therapeutic applications, these results suggested that evaluation of the expression of the unique functional isoform (ERCC1-202) constitutes a more accurate predictor of cisplatin benefit in patients with NSCLC than any other current approach. In other words, these data showed for the first time that therapeutic decision regarding cisplatin-containing treatment in patients with NSCLC requires the specific detection of the unique functional isoform of ERCC1-202.

These results explained the contradictory results obtained by the other teams so far, as none of them used antibodies that could distinguish functional ERCC1 isoform 202 from the other nonfunctional isoforms. Accordingly, it was difficult in the past to validate the correlation between the level of ERCC1 expression and overall survival on the basis of immunohistochemical detection, as abundant expression of one or several nonfunctional isoforms led to a false classification of the tumor as ERCC1-positive.

Using these unique ERCC1 deficient human NSCLC cell lines, the present Inventors further explored the influence of the different ERCC1 protein isoforms on DNA repair, protein-protein interactions and cellular mitotic process. Their data demonstrated that all currently known functions of ERCC1 are fulfilled by the same and unique ERCC1 isoform ERCC1-202 (see example 7 below).

Thus, the present invention provides an in vitro method for detecting the susceptibility of a tumor cell to a chemotherapy, said method comprising the step of measuring the expression level of the isoform 202 of the ERCC1 protein (hereafter referred to as "ERCC1-202"), for example by immunohistochemistry in a formalin-1-fixed paraffin-embedded tumor sample, by immunofluorescence on tumor cells or by mRNA analysis of tumor cell samples.

BRIEF DESCRIPTION OF THE DRAWINGS

The subject matter that is regarded as the invention may be best understood by reference to the following description taken in conjunction with the accompanying drawing figures in which:

FIG. 1A shows an example of ERCC1 staining—Image (400*) of a strongly ERCC1-positive squamous cell carcinoma (Intensity=3);

FIG. 1B shows an example of ERCC1 staining—Image (400*) of an ERCC1-negative squamous cell carcinoma with positive internal controls (arrow);

FIG. 3C shows absence of negative dominant isoform—Clonogenic growth of isoform expressing cells treated two to three weeks with low cisplatin concentrations. Table specifies cisplatin IC50 (nM) values from clonogenic growth of cells;

FIG. 5B shows ERCC1 isoforms stability and expression—Assessment by qRT-PCR of ERCC1 isoforms mRNAs in frozen samples from a series of 123 cases of resected NSCLC with matched tumour and normal specimens. The expression of ERCC1 isoform mRNA was determined using the 2-ΔΔCt method and data are presented as the fold-change in ERCC1 isoform mRNA expression relative to total ERCC1 mRNA. ERCC1-201 mRNA isoform was upregulated in tumours samples;

FIG. 8B shows ERCC1-protein complexes required ERCC1-202 isoform expression—Proximity ligation assay (PLA, Duolink) detection of ERCC1/XPF heterodimers in A549 WT and ERCC1 deficient clone 216 expressing each of the four ERCC1 isoforms.

DETAILED DESCRIPTION OF THE INVENTION

ERCC1 Isoforms

Figure 2A:
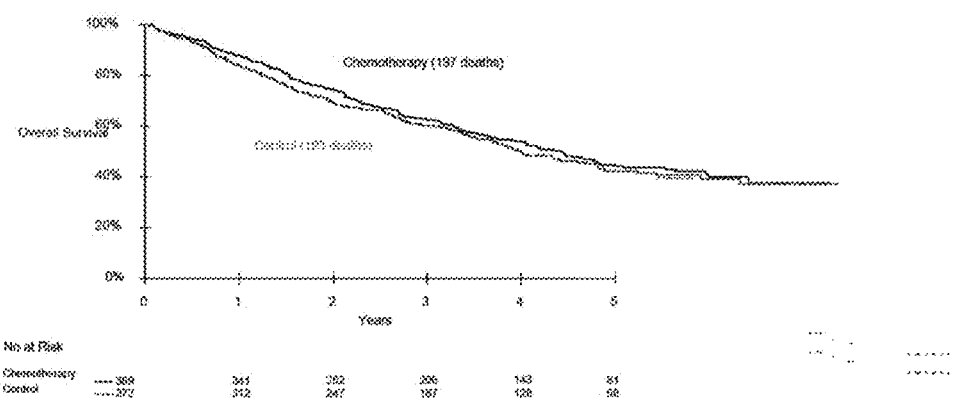
FIG. 2A shows Kaplan-Meier estimates of the proportions of surviving patients—Overall survival according to treatment in all 761 patients—The adjusted hazard ratio for death in the chemotherapy group as compared with the control group was 0.87 (95 percent confidence interval, 0.71 to 1.06, P=0.17)

ERCC1 was the first mammalian DNA repair gene to be cloned (Westerveld et al., 1984). ERCC1 gene contains 10 exons and codes for a pre-mRNA which leads by alternative splicing to four different isoforms (201, 202, 203, and 204). Very few data are available concerning the expression and role of the different ERCC1 isoforms.

The ERCC1-202 isoform is easily detectable. In human, the amino acid sequence of the ERCC1-202 isoform is for example the SEQ ID NO:2 (corresponding to the NCBI number NP_001974.1). It is encoded for example by the mRNA sequence SEQ ID NO:1 (NM_001983.3).

The alternatively spliced ERCC1-203 isoform, lacking the 72 bp of exon VIII, was first identified in 1986 (van Duin et al.). Van Duin et al. already suggested this isoform to be non-functional to repair ultraviolet (UV) light (NER) and mitomycin-C (interstrand cross-link repair—ICL-R) damages. Later, one report suggested this transcript may have a helper function for DNA repair of UV and mitomycin-C damages (Belt, 1991). In ovarian cancer tissues, highly variable splicing of ERCC1 mRNA was observed, and the alternatively spliced ERCC1-203 varied between 2 to 71% of the total ERCC1 mRNA (Dabholkar, 1994). Interestingly, the mRNA levels of this isoform were strongly inversely related to DNA repair activity, suggesting this shorter isoform to be a negative dominant of ERCC1 DNA repair function (Dabholkar, 1995; Yu, 1998). In small cell lung cancer cell line the ERCC1-203 protein isoform was found upregulated (Stordal 2009) after cisplatin exposure. This upregulation did not seem to have an influence on DNA repair efficiency in this study but the authors proposed this isoform to have a role in cell cycle arrest. Lately, ERCC1-203 isoform was confirmed to negatively affect the NER function of ERCC1 for cisplatin resistance in ovarian cancer cells (Sun et al, 2009). In human, the amino acid sequence of the ERCC1-203 isoform is for example the SEQ ID NO:6

(NP_001159521.1). It is encoded for example by the mRNA sequence SEQ ID NO:5 (NM_001166049.1).

First in mouse keratinocytes (Song et al., 2011), then in human malignant melanoma cells (Li W and Melton D W, 2011), the ERCC1-201 protein isoform was identified to be encoded by a larger ERCC1 transcript, originated from an upstream promoter. This transcript was found highly upregulated after cisplatin exposure by MAPK pathway in human melanoma cells (Li W and Melton D W, 2011). No functional analysis was accomplished about ERCC1-201 isoform but mutational analysis achieved by Sijbers et al. (1996) suggested this isoform to be non-functional. Indeed, they identified that the 91 N-terminal amino acids of ERCC1-202 isoform are dispensable for repair function, in contrast to a deletion of only four residues from the C-terminus. Since the ERCC1-201 isoform harbours an alternative C-terminus peptide sequence it is more than probable that it is non-functional with respect to NER activity. In human, the amino acid sequence of the ERCC1-201 isoform is for example the SEQ ID NO:4 (NP_973730.1). It is encoded for example by the mRNA sequence SEQ ID NO:3 (NM_202001.2).

The ERCC1-204 isoform, which lack the long 215 bp exon-3, has never been reported in the literature. This isoform still have the XPF, MSH2 and dsDNA binding domains but lack a part of the XPA and ssDNA binding domains. Thus this isoform could negatively influence DNA repair by sequestration of XPF or MSH2. In human, the amino acid sequence of the ERCC1-204 isoform is for example the SEQ ID NO:8 (NSP00000394875.2). It is encoded for example by the mRNA sequence SEQ ID NO:7 (ENST00000423698.2).

The Method of the Invention

The present invention provides in vitro methods for detecting the susceptibility of a tumor cell to a chemotherapy, said method comprising the step of measuring the expression level of the isoform 202 of the ERCC1 protein (ERCC1-202).

This expression level can be assessed either by measuring the mRNA level (e.g., by RT-PCR or by in situ hybridization or Duolink) or by measuring the protein level of this isoform, for example by means of an immunological method.

By "immunological method", it is herein meant any experimental method involving antibodies that are able to recognize specifically the isoform 202 of the ERCC1 protein. These immunological methods can be in particular an immunohistochemistry assay or an immunofluorescence assay.

In an "immunohistochemical assay", a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or P-galactosidase), or chemical methods (e.g., DAB/Substrate chromagen), gold, fluorescent or labelled antibodies by any of the many different methods known to those skilled in this art. In embodiments of the said immunohistochemical method, detection or assaying the level of the isoform 202 of the ERCC1 protein in a tumor sample includes contacting it with an antibody or antigen-binding fragments directed against said isoform or fragments thereof; and determining the amount of the binding antibody on the tumor sample.

In contrast thereto, as used herein, an "immunofluorescence assay" is a technique using fluorescence microscopy on cells that have been extracted from the tumor tissue or on cell lines, e.g., on cultured cell lines or on individual cells. This technique uses the specificity of antibodies to their antigen to target fluorescent dyes to specific biomolecule targets within a cell, and therefore allows visualization of the distribution of the target molecule (the isoform 202 of ERCC1) through the sample. Immunofluorescence can be used in combination with other, non-antibody methods of fluorescent staining, for example, use of DAPI to label DNA.

Several microscope designs can be used for immunohistochemical or immunofluorescence assays; the simplest is the epifluorescence microscope. The confocal microscope is also widely used. Various super-resolution microscope systems that are capable of much higher resolution can also be used.

As used herein, the term "antibody" includes immunoglobulin molecules and antigen binding fragments thereof. The antibody can be a polyclonal antibody or a monoclonal antibody. The antibody can be labeled by a detectable means and includes enzymatically, radioactively, fluorescently, chemiluminescently or bioluminescently labeled antibodies by any of the many different methods known to those skilled in this art.

By "antigen-binding fragments" it is intended to encompassed particularly the fragments Fv, Fab, F(ab')2, Fab', scFv, scFv-Fc. These antibody fragments are obtained using conventional techniques well-known to those with skill in the art, and the fragments are screened for utility in the same manner as are intact antibodies.

In the context of the present invention, an antibody is said to "recognize" or "bind" the ERCC1 isoform 202 of SEQ ID NO:2 if said antibody has an affinity constant $K_a$ (which is the inverted dissociation constant, i.e. $1/K_d$) higher than $10^7$ $M^{-1}$, preferably higher than $10^8$ $M^{-1}$, more preferably higher than $10^9$ $M^{-1}$ for said isoform. Also, in the context of the present invention, an antibody is said to "specifically bind" or to "specifically recognize" the ERCC1 isoform 202 of SEQ ID NO:2 if said antibody has an affinity constant $K_a$ higher than $10^7$ $M^{-1}$, preferably higher than $10^8$ $M^{-1}$, more preferably higher than $10^9$ $M^{-1}$ for said isoform and has an affinity constant $K_a$ lower than $10^5$ $M^{-1}$ for all the other proteins, including the other isoforms of ERCC1.

The affinity constant which is used to characterize the binding of antibodies (Ab) to a peptide or an antigen (Ag) is the inverted dissociation constant defined as follows:

$$Ab + Ag \rightleftharpoons AbAg$$

$$K_a = \frac{[AbAg]}{[Ab][Ag]} = \frac{1}{K_d}$$

This affinity can be measured for example by equilibrium dialysis or by fluorescence quenching, both technologies being routinely used in the art.

In a preferred embodiment, the antibody of the invention binds the ERCC1 isoform 202 of SEQ ID NO:2 with a $K_D$ of less than $10^{-9}$M, preferably of less than $10^{-10}$ M.

The present inventors have shown that only the 202 isoform of ERCC1 can form stable heterodimer complexes with the DNA repair endonuclease XPF (SEQ ID NO: 9, corresponding to NP_005227.1, which is encoded by the ERCC4 gene), with the XPA protein (SEQ ID NO:10, corresponding to NP_000371.1), with the DNA mismatch repair protein MSH2 (SEQ ID NO: 11 corresponding to the isoform 1 (full length) NP_000242.1 or SEQ ID NO: 12 corresponding to the isoform 2 NP_001245210.1), with the Fanconi anemia Group G protein FANC G (SEQ ID NO: 13, corresponding to NP_004620.1), with the SLX4 protein (SEQ ID NO:14 corresponding to NP_115820.2), with the kinesin Eg5 (SEQ ID NO: 15, corresponding to NP_004514.2 encoded by the KIF11 gene), with the MAD2A protein (SEQ ID NO: 16, corresponding to NP_002349.1 encoded by the MAD2L1 gene), and the protein TRF2 (SEQ ID NO: 17, corresponding to NP_005643.2, encoded by the TERF2 gene).

Their data clearly suggest that detecting the presence of ERCC1/XPF, ERCC1/XPA, ERCC1/MSH2, ERCC1/FANCG, ERCC1/SLX4, ERCC1/Eg5, ERCC1/MAD2A, or of ERCC1/TRF2 heterodimers is helpful for quantifying the level of functional ERCC1-202 isoform in cancer cell.

Consequently, the detecting method of the invention may comprise the step of detecting and/or quantifying the presence of a stable heterodimers selected from the group consisting of: ERCC1/XPF, ERCC1/XPA, ERCC1/MSH2, ERCC1/FANCG, ERCC1/SLX4, ERCC1/Eg5, ERCC1/MAD2A, and ERCC1/TRF2. This detection/quantification may be performed by conventional means, such as protein complex immunoprecipitation, pull-down assays, Proximity ligation assay (PLA), FRET assays, surface plasmon resonance (SPR) assays, affinity capture mass spectrometry or the Duolink® immunoassay developed by Olink. Immunoassays such as immunoprecipitation, pull-down assays and the Duolink® assay are herein preferred. Proximity ligation assay (PLA) is even more preferred.

In one embodiment, the skilled person will preferably use an antibody which binds specifically to the XPF protein, for example the anti-XPF antibody clone 3F2/3; or an antibody which binds specifically to the XPA protein, for example the anti-XPA antibody clone 5A2 commercialized by Pierce under the reference "MA1-21460"; or an antibody which binds specifically to the MSH2 protein, for example the anti-MSH2 antibody commercialized by BIORBYT under the reference "orb16010"; or an antibody which binds specifically to the FANCG protein, for example the anti-FANCG antibody commercialized by Abcam under the reference "ab54645"; or an antibody which binds specifically to the Eg5 protein, for example the anti-Eg5 antibody commercialized by Abcam under the reference "ab51976"; or an antibody which binds specifically to the SLX4 protein, for example the anti-SLX4 antibody commercialized by Abnova under the reference "H00084464"; or an antibody which binds specifically to the MAD2A protein, for example the anti-MAD2A antibody clone 17D10 commercialized by Abcam under the reference "10691"; or an antibody which binds specifically to the TRF2 protein, for example the anti-TRF2 antibody clone 4A794 commercialized by Abcam under the reference "ab13579".

In another embodiment, the skilled person will preferably use an antibody which binds specifically to the ERCC1—XPF heterodimer, the ERCC1/XPA heterodimer, the ERCC1/MSH2 heterodimer, the ERCC1/FANCG heterodimer, the ERCC1/SLX4 heterodimer, the ERCC1/Eg5 heterodimer, the ERCC1/MAD2A heterodimer, and the ERCC1/TRF2 heterodimer.

In the method of the present invention, the antibody recognizing ERCC1-202 is preferably selected in the group consisting of: the mouse monoclonal antibody clone 8F1 (Thermo Scientific Inc. ERCC1 Ab-2 Cat. MS-671-P1), the mouse monoclonal antibody 3H11 (Novus Biologicals Cat. NB100-117 or Santa Cruz Biotechnology Inc. Cat. sc53281), the rabbit polyclonal antibody FL297 (Santa Cruz Biotechnology Inc. Cat. sc-10785), the rabbit monoclonal antibody EP2143Y (Origene Inc. Cat. TA306972), the mouse monoclonal antibody 4F9 (Origene. Inc. Cat. UM500008), and the mouse monoclonal antibody 2E12 (Origene. Inc. Cat. UM500011).

Interestingly, the method of the present invention can be carried out on post-operative patient tumor samples. The chemotherapy will then be applied after a surgical resection of the tumor.

In a preferred embodiment of the invention, the in vitro method of the invention is thus for detecting susceptibility to a chemotherapy of a tumor cell from patients who had undergone a surgical resection of their tumor.

The method of the invention enables to predict if a platinum-based chemotherapy will be of beneficial use in patients suffering from cancer. As a matter of fact, the present inventors demonstrated that the expression level of ERCC1-202 impacts the efficiency of a platinum-based chemotherapy treatment. In particular, their results suggest that, when the expression level of ERCC1-202 is low, then platinum-based chemotherapy will be efficient and said patient will experience long survival upon treatment with this platinum-based chemotherapy. Conversely, when the expression level of ERCC1-202 is high, then a platinum-based chemotherapy will be useless because the patient's survival will not increase upon treatment with this platinum-based chemotherapy. In this case, a platinum-based chemotherapy is to be avoided and another treatment is to be preferred (for example, surgery, immunotherapy, radiotherapy, platinum-free chemotherapy, etc.).

Thus, in another aspect, the present invention relates to a method for treating a patient suffering from cancer, containing the steps of:
  i) detecting the susceptibility of the tumor cells of said patient to a chemotherapy by means of the measuring the ERCC1-202 expression level as disclosed above, and
  ii) if said tumor cells express low level of ERCC1-202, then administering to said patient an efficient dose of a platinum-based chemotherapy, whereas
  if said tumor cells express high level of ERCC1-202, then treating said patient with a platinum-free chemotherapy, by surgery, by radiotherapy, or by immunotherapy.

Determining if the expression level of ERCC1-202 is low or high in a tumor sample can be performed by comparing the expression level of ERCC1-202 in said sample with the expression level of ERCC1-202 obtained in an internal positive control which is used as a reference. Immunostaining intensity is for example multiplied by a proportion score (representative of the percentage of positive tumor nuclei) to obtain a final quantitative H-Score (for "Histology-score"). The median value of the H-Scores was a priori chosen as the cut-off point.

In immunohistochemical assays, high levels of ERCC1-202 are for example detected when the H Score exceeding median value of H-Score (i.e., tumors with a staining intensity score of 2 and with 50% or more positive nuclei or with a staining intensity score of 3 and 10% or more positive nuclei). Low levels of ERCC1-202 are detected for example when the H-Score is below the median value of H-Score. In Duolink assays, expression level of ERCC1-202 is obtained by assessing the number of fluorescent points in the nuclei of tumoral cells.

Preferably, internal positive control herein consists of stroma cells surrounding the tumor area.

In a preferred embodiment of the invention, the method is based on an immunohistochemical assay comprising the following steps:
- (a) obtaining slides from formalin-fixed paraffin-embedded tumor samples,
- (b) retrieving epitope in buffer,
- (c) incubating slides with a monoclonal ERCC1 antibody recognizing specifically the isoform 202 of ERCC1,
- (d) determining the amount of binding antibodies on the formalin-fixed paraffin-embedded tumor samples, using the amount of binding antibodies on an internal positive control as a reference,
- (e) determining the percentage of labeled nuclei on the formalin-fixed paraffin-embedded tumor samples,
- (f) multiplying the value estimated in step (d) with the value estimated in step
- (e), and
- (g) determining a platinum-based chemotherapy regimen by comparing the value obtained in step (f) to a pre-determined threshold level.

With this method, steps (d) and (f) are used for the first time. They make the detection of ERCC1 surprisingly quantitative and reproducible.

In a more preferred embodiment of the invention, such cancer is preferably a non-small-cell lung cancer.

In another preferred embodiment of the invention, the cancer chemotherapy is a platinum-based cancer chemotherapy.

It is also preferred that the cancer chemotherapy is based on cisplatin alone or associated with other chemotherapeutic agents as etoposide or a vinca alkaloid.

The invention also relates to a kit for the detection or quantification of the isoform 202 of the ERCC1 protein (ERCC1-202), wherein said kit comprises antibodies and appropriate reagents and buffers. The antibody used in this kit is the monoclonal ERCC1 mouse antibody clone 8F1 commercialized by Neomarkers, the mouse monoclonal antibody 3H11 (distributed by several manufacturers), the rabbit polyclonal antibody FL297 (Santa Cruz), or the rabbit monoclonal antibody EP2143Y (distributed by several manufacturers).

In a preferred embodiment, said detection kit is used for detecting the susceptibility of a tumor cell to a chemotherapy, for example in the method described above, or in a method for treating a patient suffering from cancer, for example in the method described above.

EXAMPLES

Example 1

Materials and Methods

Patients and Study Design.

All patients had participated in the IALT study that compared adjuvant cisplatin-based chemotherapy to observation in patients with non-small-cell lung cancer. Inclusion criteria and the results of the IALT have already been reported (The International Adjuvant Lung Cancer Trial Collaborative Group. Cisplatin-based adjuvant chemotherapy in patients with completely resected non-small-cell lung cancer. N Engl J Med 2004; 350:351-60), see table 1. Briefly, 1,867 patients with completely resected stage I-III non-small-cell lung cancer had been randomized to either chemotherapy with cisplatin (total dose 300-400 mg/m$<$2$>$) plus another drug (etoposide or a vinca alkaloid), or observation (control group). The median follow-up time was 56 months.

The IALT-Bio study was subsequently designed by a steering committee to examine whether immunohistochemically assessed tumor markers had the ability to predict a survival benefit from chemotherapy in formalin-fixed paraffin-embedded tumor samples collected from centers that had recruited more than 10 patients. To study whether the effect of chemotherapy was different between patients with a positive or a negative marker status, the estimated power to detect a 20 percent difference in the survival benefit at 5 years in 800 patients was 66 percent (two-sided, type I error 1%). Twenty-eight centers in 14 countries (see table 1) contributed specimens.

Approval was obtained from the local Institutional Review Boards according to the legal regulations in each participating country.

All tumors were reviewed centrally (Brambilla E, Lantuejoul S, Dunant A, et al. IALT—International Adjuvant Lung Cancer Trial—: Quality assessment and histopathological review according to the WHO 2004 classification and assessment of prognostic and predictive role of pathological criteria. *Lung Cancer* 2005; 49. Suppl. 2:S44) according to the W.H.O. 2004 histo-pathological classification.

TABLE 1

| The IALT-Bio participating centers (investigators and pathologists) | |
|---|---|
| AUSTRIA: | R. Pirker, Internal Medicine I, Vienna, G. Dekan, Institute of Pathology, Vienna |
| BELGIUM: | J. Vansteenkiste, University Hospital, Leuven |
| BRAZIL: | I. Sathler Pinel, Instituto Nacional de Cancer, Rio de Janeiro |
| | R. Younes, Hospital A.C. Camarco, Sao Paulo |
| FRANCE: | A.A. Kanoui, Centre Physiothérapie du Rouget, Sarcelles; |
| | R. Dachez, Laboratoire L.C.L., Paris; |
| | S. Deslignères, Hospital Delafontaine, Saint-Denis; |
| | O. Languille-Mimoune, Cabinet Pathologie, Paris; |
| | P. Sabatier, Centre Hospitalier Victor Dupouy, Argenteuil |
| | T. Le Chevalier, Institut Gustave-Roussy, Villejuif; |
| | M. Antoine, Hôpital Tenon, Paris |
| | P. Boz, Cabinet de Pathologie, Papeete; |
| | P. Bruneval, Association Promotion Anatomie Pathologique, Paris; |
| | M.C. Charpentier, Cabinet Pathologie Tolbiac, Paris; |
| | B. Chetaille, Hôpital Sainte Marguerite, Marseille; |
| | E. Dulmet, Centre Chirurgical Marie-Lannelongue, Le Plessis Robinson; |
| | F. Capron, Groupe Hospitalier Pitié-Salpétrière, Paris; |
| | B. Gosselin, C.H.U., Lille; |

TABLE 1-continued

The IALT-Bio participating centers (investigators and pathologists)

|  |  |
|---|---|
|  | D. Grunenwald, P. Validire, Institut Mutualiste Montsouris, Paris; |
|  | F. Labrousse, C.H.U., Limoges; |
|  | N. Pericoli, Roma (Italy); |
|  | D. Petrot, Cabinet d'Anatomie Pathologique, Niort; |
|  | N. Rouyer, Cabinet de Pathologie Butet-Rouyer, Nice |
|  | B. Milleron, M. Antoine, Hôpital Tenon, Paris |
|  | J.F. Morère, M. Kambouchner, Hôpital Avicenne, Bobigny |
|  | G. Ozenne, Ceditrac—CMC du Cèdre, Bois Guillaume |
|  | T. Ducastelle, Laboratoire d'Anatomie et Cytologie, Rouen |
|  | E. Quoix, Hôpital Lyautey, Strasbourg; |
|  | P. Durand de Grossouvre, Laboratoire d'Anatomie Pathologique, Haguenau; |
|  | B. Gasser, C.H.U., Strasbourg |
|  | A. Riviére, Centre François Baclesse, Caen; |
|  | F. Galateau-Salle, CHU, Caen |
|  | C. Tuchais, P. Janet, G. Bertrand, I. Valo, Centre Paul Papin, Angers |
| GERMANY: | W. Eberhardt, University Hospital, Essen; |
|  | D. Theegarten, Institute of Pathology, Ruhr-University Bochum, Bochum |
| GREECE: | P. Christaki, Papanikolaou General Hospital, Pylea |
|  | T. Dosios, V. Kyriakou, Athens University School of Medicine, Athens |
|  | E. Papadakis, P. Agelidou, Sotiria Hospital, Athens |
|  | K. Zarogoulidis, University Hospital, Thessaloniki |
| ITALY: | A. Masotti, Azienda Ospedaliera Di Verona, Verona |
| LITHUANIA: | A. Jackevicius, Institute of Oncology Vilnius University, Vilnius |
| POLAND: | J. Laudanski, L. Chyczewski, M. Kozlowski, J. Niklinski, Medical School, Bialystok |
|  | T. Grodski, J. Pankowski, Regional Hosp. For Lung Diseases, Szczecin |
|  | T. Orlowski, M. Chabowski, R. Langfort, Institute of Tuberculosis and Lung Disease, Warsaw; |
|  | B. Muszczynska-Bernhard, Dolnoslaskiego Centrum Chorob Pluc, Wroclaw |
| ROMANIA: | T. Ciuleanu, Oncological Institute "Ion Chiricuta", Cluj-Napoca |
| SLOVAKIA: | J. Baumohl, University Teach. Hospital, Kosice |
| SPAIN: | F. Cardenal, Hospital Duran I Reynals, Barcelona; R. Bernat, Hospital de Bellvitge, Barcelona |
|  | J. Salinas, J.B. Lopez, Hospital Virgen de Arrixaca, El Palmar Murcia |
| SWEDEN: | B. Bergman, A. Hussein, Sahlgrenska Hospital, Göteborg |
| YUGOSLAVIA: | G. Radosavljevic, Institute for Lung Disease, Belgrade |

Immunostaining for ERCC1.

The epitopes were first retrieved in citrate buffer (10 mM, pH 6.0, heated for 30 minutes in a bain marie), then slides were incubated at a 1:300 dilution over 60 minutes with the monoclonal ERCC1 mouse antibody (clone 8F1, NeoMarkers, Fremont Calif., USA) that was raised against the full-length human ERCC1 protein. Antibody binding was detected by means of an ABC-kit with NovaRED™ as the substrate (Vectastain Elite, Vector Laboratories, Burlingame Calif., USA) and Mayer's hematoxylin as the counterstain. Sections of normal tonsil tissues were included as external positive controls and stromal cells (endothelium) surrounding the tumor area served as internal positive controls.

Microscopic Analysis

Two investigators who where blinded to clinical data, independently evaluated ERCC1 staining under the light microscope at *400 magnification. We recorded whether or not tumor or stromal cells expressed ERCC1. In addition, staining intensity was graded on a scale of 0 to 3 (using endothelial cells in tonsil controls as a reference point [intensity 2]). Discordant cases were reviewed. Cases without valid internal controls were excluded. Five images of representative areas were acquired at *400 magnification for each case. All positive or negative tumor nuclei (a total of 500-1,500 tumor nuclei per case) were manually counted on a computer screen using ImageJ freeware edited by the National Institutes of Health (http://rsb.info.nih.gov/ij). The percentage of positive tumor nuclei was calculated per case and a proportion score was attributed (0 if 0 percent; 0.1 if 1 to 9 percent; 0.5 if 10 to 49 percent; 1.0 if 50 percent or more), as previously described (Al Haddad S, Zhang Z, Leygue E, et al. Psoriasin (S100A7) expression and invasive breast cancer. Am J Pathol 1999; 155:2057-66 or Handra-Luca A, Bilal H, Bertrand J C, Fouret P. Extra-cellular signal-regulated ERK-1/ERK-2 pathway activation in human salivary gland mucoepidermoid carcinoma: association to aggressive tumor behavior and tumor cell proliferation. Am J Pathol 2003; 163:957-67). In each case, the proportion score was multiplied by the staining intensity of nuclei to obtain a final quantitative H-score (among 9 possible ones). The median value of the H-scores was a priori chosen as the cut-off point for separating ERCC1-positive from ERCC1-negative tumors.

Statistical Analysis.

As in the IALT, the primary endpoint was overall survival after the date of randomization. Disease-free survival was analyzed as a secondary endpoint. In order to study selection bias within the IALT-Bio participating centers, the pre-randomization characteristics and overall survival of the two groups of patients (with or without blocks) were compared using a Cox model. Baseline data according to the ERCC1 status were compared in univariate analyses with Chi-square tests and with a multivariate logistic model.

Survival rates were estimated using the Kaplan-Meier method. The predictive values of the ERCC1 status and chemotherapy for survival were studied using the Cox model. As in the IALT analysis, the Cox model included every factor used in the stratified randomization (center, disease stage, and type of surgery), plus clinical and histological predictive factors (age, sex, W.H.O. performance status, and revised histopathological type). All other factors that were statistically related to the ERCC1 status in the multivariate logistic model (P<0.05) were added to the survival Cox model (pathological T status, and pleural invasion). The predictive value of ERCC1 was studied by testing the interaction between the ERCC1 status and the attributed treatment (chemotherapy or no chemotherapy) in the same Cox model. All reported P values were two-sided. P values below 0.01 were considered statistically significant in order to limit the risk of false positive results. All analyses were performed using SAS software, version 8.2.

Example 2

Patient Characteristics

The 28 centers which participated in the IALT-Bio study included 1045 patients in the original IALT study. They were able to provide one tumor block for only 867 patients (83 percent). These 867 patients were comparable to the remaining 178 in terms of pre-randomization characteristics and overall survival. The amount and quality of the 824 blocks were adequate for serial sectioning. Among these blocks, 783 contained tumor material corresponding to non-small-cell lung cancer and were included in the IALT-Bio study. After exclusion of cases without valid positive internal controls, ERCC1 expression was evaluated in 761 cases. All further statistical analyses were based on these 761 patients.

The characteristics of the IALT-Bio study patient population are summarized in Table 1. A total of 426 cases were squamous-cell carcinomas (56 percent), 242 adenocarcinomas (32 percent), and 93 were of another histological type (12 percent). Median age was 58 years (range 27-77) and the great majority were males (81.6 percent). Three hundred and eighty-nine patients (51 percent) were randomized to receive adjuvant cisplatin-based chemotherapy, whereas 372 (49 percent) were randomized to the control group.

Example 3

Immunohistochemically Assessed ERCC1 Expression

As illustrated in FIG. 1, ERCC1 immunostaining was nuclear. The median value of the percentage of stained cells was 24 percent (range 0 to 100 percent), whereas the median value of H-scores was 1.0 Tumors with an H-score exceeding 1.0 (i.e. tumors with a staining intensity score of 2 and 50 percent or more positive nuclei or a staining intensity score of 3 and 10 percent or more positive nuclei) were deemed ERCC1 positive, which was the case in 335 patients (44 percent). The median H-score alone (1.0) was attributed to 164 tumors (22 percent). The main differences in clinicopathological parameters according to ERCC1 expression are reported in Table 2 (univariate analysis). Using the multivariate logistic model, ERCC1 expression was significantly correlated with age (P=0.02 lower in young patients), sex (P=0.04 lower in females), pathological T status (P=0.04 lower with a higher T status), histological type (lower in adenocarcinomas P<0.0001), and pleural invasion (P=0.01 higher in the case of pleural invasion).

TABLE 2

Patient Characteristics

| Characteristic | Total N = 761 (percent) | ERCC1+ N = 335 (percent) | ERCC1− N = 426 (percent) | P-value* |
|---|---|---|---|---|
| Age | | | | P < 0.003 |
| <55 yr | 231 (30) | 80 (24) | 151 (35) | (P for trend: P < 0.008) |
| 55-64 yr | 330 (43) | 161 (48) | 169 (40) | |
| >64 yr | 200 (26) | 94 (28) | 106 (25) | |
| Sex | | | | P < 0.0005 |
| Male | 621 (82) | 292 (87) | 329 (77) | |
| Female | 140 (18) | 43 (13) | 97 (23) | |
| Pathological TNM stage | | | | P = 0.97 |
| Stage I | 267 (35) | 119 (35) | 148 (36) | |
| Stage II | 175 (23) | 76 (23) | 99 (23) | |
| Stage III | 319 (42) | 140 (42) | 179 (42) | |
| T of TNM | | | | P = 0.10 |
| 1 | 118 (16) | 60 (18) | 58 (14) | |
| 2 | 452 (59) | 188 (56) | 264 (62) | |
| 3 | 181 (24) | 85 (25) | 96 (23) | |
| 4 | 10 (1) | 2 (1) | 8 (2) | |
| Histological type | | | | P < 0.0001 |
| Squamous cell carcinoma | 426 (56) | 236 (70) | 190 (45) | |
| Adenocarcinoma | 242 (32) | 71 (21) | 171 (40) | |
| Other | 93 (12) | 28 (8) | 65 (15) | |
| Performance Status | | | | P = 0.06 |
| 0 | 426 (56) | 188 (56) | 238 (56) | |
| 1 | 276 (36) | 113 (34) | 163 (38) | |
| 2 | 59 (8) | 34 (10) | 25 (6) | |
| Pleural invasion | | | | P < 0.007 |
| Yes | 61 (8) | 37 (11) | 24 (6) | |
| No | 700 (92) | 298 (89) | 402 (94) | |
| Vascular invasion | | | | P = 0.04 |
| Yes | 222 (29) | 85 (25) | 137 (32) | |
| No | 539 (71) | 250 (75) | 289 (68) | |
| Surgery | | | | P = 0.35 |
| Pneumonectomy | 306 (40) | 141 (42) | 165 (39) | |
| Segment-/lobectomy | 455 (60) | 194 (58) | 261 (61) | |
| Radiotherapy | | | | P = 0.35 |
| Yes | 199 (26) | 82 (24) | 117 (27) | |
| No | 562 (74) | 253 (76) | 309 (73) | |
| Planned cisplatin dose | | | | P = 0.67 |
| 80 mg/m² per cycle | 139 (18) | 58 (17) | 81 (19) | |
| 100 mg/m² per cycle | 544 (71) | 245 (73) | 299 (70) | |
| 120 mg/m² per cycle | 78 (10) | 32 (10) | 46 (11) | |

TABLE 3

Variation of overall survival according to attributed treatment and ERCC1 status

| | Chemotherapy | Control group | All patients | Adjusted Hazard ratio for death (chemotherapy vs. controls) [95% CI] |
|---|---|---|---|---|
| ERCC1-negative tumors | 105/224 47% [40%-55%] 56 months * | 113/202 39% [32%-47%] 42 months * | 218/426 44% [38%-49%] 48 months * | 0.67 [0.51-0.89] P < 0.006 |
| ERCC1-positive tumors | 92/165 40% [32%-49%] 50 months * | 80/170 46% [37%-55%] 55 months * | 172/335 43% [37%-49%] 52 months * | 1.18 [0.87-1.61] P = 0.29 |

TABLE 3-continued

Variation of overall survival according to attributed treatment and ERCC1 status

|  | Chemotherapy | Control group | All patients | Adjusted Hazard ratio for death (chemotherapy vs. controls) [95% CI] |
|---|---|---|---|---|
| All patients | 197/389<br>44% [39%-50%]<br>53 months * | 193/372<br>42% [37%-48%]<br>48 months * | 390/761<br>43% [39%-47%]<br>50 months * | 0.87<br>[0.71-1.06]<br>P = 0.17 |
| Adjusted Hazard ratio for death (ERCC1 positive vs. ERCC1 negative) [95% CI] | 1.15<br>[0.85-1.56]<br>P = 0.38 | 0.65<br>[0.48-0.89]<br>P < 0.008 | 0.87<br>[0.69-1.09]<br>P = 0.23 | Test for interaction ERCC1*treatment<br>P < 0.009 |

CI denotes confidence interval
the central cells denoted by * contain the following information: number of deaths, number of patients, 5-year survival rate and the 95 percent confidence interval, and median survival.

Example 4

Overall Survival and ERCC1 Expression

The 5-year overall survival rate was 43 percent, 95 percent confidence interval [39 to 47 percent] (Table 3) for the total study-population. Using the Cox model, ERCC1 expression had no predictive value for the entire study population (adjusted hazard ratio for death, 0.87; 95 percent confidence interval [0.69 to 1.09], P=0.23).

Example 5

Overall Survival and Adjuvant Chemotherapy

The 5-year overall survival rates were 44 percent (95 percent confidence interval [39 to 50 percent]) and 42 percent (95 percent confidence interval [37 to 48 percent]) in the chemotherapy group and control group respectively (Table 3). In the Cox model, the adjusted hazard ratio for death was 0.87 (95 percent confidence interval [0.71 to 1.06], P=0.17) in favor of chemotherapy (Table 3, FIG. 2A).

Example 6

Benefit of Adjuvant Chemotherapy According to ERCC1 Expression

Figure 2B:
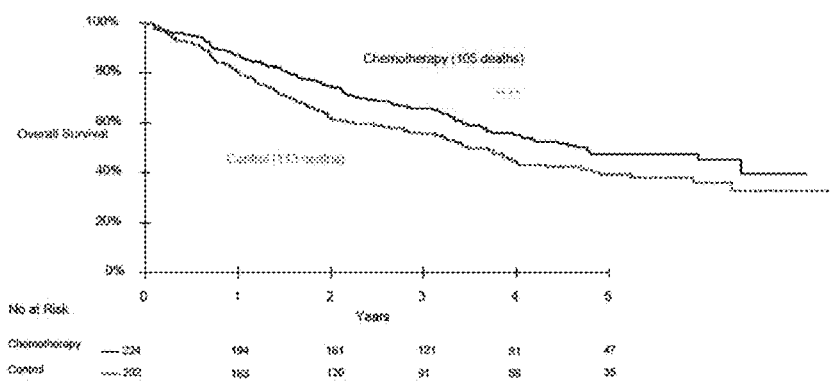
FIG. 2B shows Kaplan-Meier Estimates of the proportions of surviving patients—Overall survival according to treatment in patients with ERCC1-negative tumors—The adjusted hazard ratio for death in the chemotherapy group as compared with the control group was 0.67 (95 percent confidence interval, 0.51 to 0.89, P<0.006)
Figure 2C:
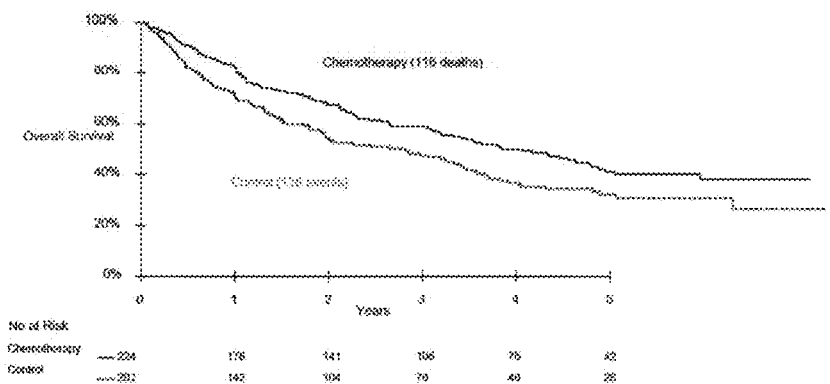
FIG. 2C shows Kaplan-Meier Estimates of the proportions of surviving patients—Disease-free survival according to treatment in patients with ERCC1-negative tumors. The hazard ratio for disease progression or death was 0.69 (95 percent confidence interval, 0.53 to 0.90, P<0.007)

The interaction term between ERCC1 expression and treatment was statistically significant (for overall survival, P<0.009). In patients with ERCC1-negative tumors, overall survival was significantly higher in the chemotherapy group compared to the control group (adjusted hazard ratio for death, 0.67; 95 percent confidence interval [0.51 to 0.89] P<0.006) (Table 3). The 5-year survival rates were 47 percent (95 percent confidence interval [40 to 55 percent]) and 39 percent (95 percent confidence interval [32 to 47 percent]) respectively. Median overall survival was 14 months longer in the adjuvant chemotherapy group compared to the control group of patients with ERCC1-negative tumors (56 and 42 months respectively, FIG. 2B). Disease-free survival in patients with ERCC1-negative tumors was also significantly higher in the chemotherapy group compared to patients randomized to observation (adjusted hazard ratio for recurrence or death, 0.69; 95 percent confidence interval [0.53 to 0.90], P<0.007) (FIG. 2C).

Figure 2D:
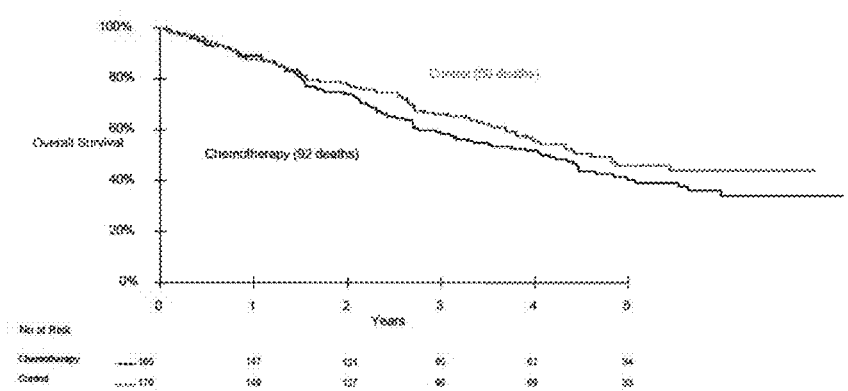
FIG. 2D shows Kaplan-Meier Estimates of the proportions of surviving patients—Overall survival according to treatment in patients with ERCC1-positive tumors. The adjusted hazard ratio for death in the chemotherapy group as compared with the control group was 1.18 (95 percent confidence interval, 0.87 to 1.61, P=0.29)

There was no survival difference between the adjuvant chemotherapy group and the control group among patients with ERCC1-positive tumors (adjusted hazard ratio for death, 1.18; 95 percent confidence interval [0.87 to 1.61], P=0.29) (Table 3, FIG. 2D).

When the analysis focused exclusively on patients in the control group, the 5-year overall survival rate was significantly higher in patients with ERCC1-positive tumors (46 percent, 95 percent confidence interval [37 to 55 percent]) than in patients with ERCC1-negative tumors (39 percent, 95 percent confidence interval [32 to 47 percent]), with an adjusted hazard ratio of 0.65, 95 percent confidence interval [0.48 to 0.89], P<0.008 (Table 3).

Example 7

Alternative roles for ERCC1 beyond NER are still currently emerging. It is now well established that ERCC1 is an important factor for DNA interstrand cross-link repair (ICL-R) (Usanova et al 2010), as well as for DNA double-strand breaks (DSB) repair via HR (homologous recombination) subpathway SSA (single-strand annealing) (Motycka, 2004), also via NHEJ (non-homologous end-joining) subpathway MMEJ (microhomology-mediated end-joining) (Ahmad 2008; De Silva I. U. et al, 2002; Sargent et al, 2000) and via activation of the FA (Fanconi anemia) pathway by permitting FANCD2 focus formation (McCabe 2008, Naim 2013). ERCC1/XPF also acts to limit non-LTR retrotransposition (Gasior 2008).

To achieve all these functions the ERCC1/XPF complex interacts with a wide range of partners. ERCC1 is catalytically inactive but indispensable for the activity of the complex and regulates DNA-/protein-protein interactions, whereas XPF provides the endonuclease activity and is involved in DNA binding and additional protein-protein interactions (see McNeil and Melton 2012 for review). ERCC1 interacts directly with XPA (xeroderma pigmentosum group A) (Li™, 1994) and MAD2A (Mitotic arrest deficient 2) (Fung, 2008) for NER, MSH2 (MutS protein homolog 2) (Lan, 2004) and FANCG (Fanconi anemia complementation group G) for ICL-R (Wang and Lambert, 2010). XPF binds to RPA (replication protein A) for NER (Bessho, 1997; Fisher, 2011), TRF2 (telomeric repeat-binding factor 2) for telomere maintenance (Zhu, 2003; Wu 2008), SLX4/BTBD12 (BTB domain-containing protein 12) for ICL-R (Svendsen 2009; Munoz 2009) and RAD52 for SSA (Motycka, 2004). Importantly, the pharmacological inhibition of the ERCC1/XPF interaction leads to increased therapeutic effect from alkylating agents such as cisplatine in cancer cells (Jordheim, 2013).

A non-repair related role for ERCC1 was also proposed in mitosis process. Studies reported that cells from ERCC1-deficient mice harboured increased genome instability, chromosome aberrations, multinucleation, enlarged nuclei with various degrees of ploidy, disruptions in cell cycle, a decrease rate of cell proliferation, and cytoplasmic morphologic modifications (Weeda, 1997; Melton, 1998; Chipchase, 2002). Recently, ERCC1 knockdown in human cells confirmed these observations independently of XPF (Rageul, 2011) or linked to XPF and kinesin Eg5 binding (Li Jing Tan 2012). Although, it is unclear if the ERCC1 impact on mitosis process is dependent or not on ERCC1 DNA-repair functions since unrepaired endogenous DNA damage could lead to these types of abnormal cellular morphology.

ERCC1 knockout cells have been widely studied from mice and CHO (Chinese hamster ovary) cells and gave important knowledge about ERCC1 functions and alternative roles beyond NER but a human ERCC1 knockout cell line had never been reported. Using Zinc-finger targeting nucleases, our group established the first model of human cancer cells ERCC1-deficient. We recently published the establishment of these A549 (lung carcinoma human cell line) ERCC1-deficient cells that displayed a high sensitivity to cisplatin accompanied with a low rate of cisplatin DNA-adduct repair by NER (Friboulet NEJM 2013). We identified that only the reintroduction of the ERCC1-202 isoform rescued NER activity and capacity to counteract cisplatin treatment (Friboulet et al, NEJM2013). These data provided important insight into the relative function of the four ERCC1 isoforms for removal of cisplatin DNA-adducts and the way they might influence patient survival.

Since the four isoforms are expressed in human samples, we tempted here to elucidate the implication of these different ERCC1-isoforms on ERCC1 functions beyond NER and DNA repair. We searched for negative dominant isoform, we analysed the interactions between ERCC1 isoforms and previously identified ERCC1-interacting partners, we examined their cellular localization and finally we investigated the influence of each isoform on the cellular mitotic process.

Materials and Methods
RNA Extraction and Quantitative Reverse Transcriptase PCR (qRT-PCR)

For ERCC1 isoform mRNA analysis we used frozen patient samples from the CHEMORES initiative (Chemotherapy resistance consortium) previously published (Friboulet, 2011).

The RNA extraction was performed with Qiagen RNeasy Mini Kit (74004; Qiagen). Total RNA (1 µg) was reverse-transcribed using the MuIV reverse transcriptase (Applied Biosystems). We designed specific TaqMan primers and probes for the different ERCC1 transcripts (sequences previously published) (Friboulet NEJM 2013). The relative expression of ERCC1 isoform mRNA was determined using the Ct value and the 2-ΔΔCt method. The data were presented as the fold-change in gene expression normalized to total ERCC1 mRNA.

Cell Lines and Proliferation Assays

Cells were grown in DMEM medium (Gibco-Invitrogen) supplemented with 10% fetal calf serum (FCS). Two different tests were used to assess cell viability:

The clonal growth of NSCLC cells was assessed by plating 500 and 1000 cells per well in six-well plates treated with low concentrations of cisplatin (50 to 2000 nM) for 2 to 3 weeks. Cell colonies were stained with a solution of crystal violet in methanol. Dried plates were then scanned and digitized to allow optical magnification and precise quantification of well area stained.

Alternatively, the cell proliferation was determined in a short-term assay based on the reduction of WST-1 (water-soluble tetrazolium salt) (Roche Molecular), after 48 hours of treatment with various concentrations of cisplatin (from 0.2 to 40 µM) and mitomycin-C (from 0.75 to 100 nM) and the IC50 was determined.

Cell Cycle and DNA Content

To study effect of cisplatin on cell cycle arrest, cells were treated with 30 nM or 300 nM of cisplatin for 48 h. For high DNA content analysis, cells were blocked in G2/M cell cycle phase with Karyomax colcemid solution (Gibco-Invitrogen) at 0.1 µg/ml for 6 h.

DNA content was determined in ethanol-fixed cells, stained with propidium iodide and analyzed using a Becton Dickinson FACScalibur flow cytometer and the CellQuest Pro software.

Cell Protein Extraction and Western Blot Analysis

Proteins were extracted by lysis in RIPA buffer (50 mM Tris, 150 mM NaCl, 5 mM EDTA, 0.5% sodium deoxycholic acid, 0.5% NP-40, 0.1% SDS) supplemented with a protease inhibitor cocktail (Complete; Roche Molecular). For nucleus and cytoplasm protein, a first extraction and separation was done with a buffer containing 10 mM HEPES, 10 mM KCl, 1 mM DTT, 1 mM PMSF and protease inhibitor cocktail supplemented with 0.3% NP40. The nucleus fraction was next resuspended in a buffer containing 20 mM HEPES and 400 mM NaCl. Protein were then separated by SDS-PAGE and transferred to nitrocellulose membranes by the iBlot® 7-Minute Blotting System (Invitrogen). Blots were incubated with primary and secondary peroxidase-conjugated antibodies and chemiluminescent detection was done using the Dura HRP Substrate (Thermo scientific).

The antibodies used were ERCC1-3H11 (sc53281; Santa Cruz), XPF-3F2, TRF2, FANCG, Lamin-B1, Eg5, MAD2A (ab85140, ab13579, ab54645, ab16048, ab51976, ab10691; abcam), ERCC1-8F1 (MS-671P1; MM France), SLX4 (H00084464; abnova), XPA (MA1-21460; pierce), MSH2 (orb16010; BIORBYT), MMS19 (66049; proteintech) and β-actin or β-tubulin antibodies (A5441, T8328; Sigma-Aldrich) for loading controls.

Diff Quik Stain

For cells morphology study, cells were fixed and stained with Diff Quik kit (130832; DadeBehring/Siemens) according to the manufacturer's instructions.

Treatments of Cells with Pharmacological Reagents

For proteasome inhibition, cells were treated with MG132 (Merck) at 2 µM for 24 h.

For video microscopy, cells were first stained with cell tracker green 2.5 µM for 30 min (C2925; Invitrogen) and then stained with Hoechst 1/8000 (62249SPCL; thermo scientific).

α and γ Tubulin Immunofluorescence Staining

Microtubules were first stabilized in PHEM buffer and then cells were fixed and permeabilized in cold methanol for 5 min. After washing with PBS 0.1% Tween, and with IFF buffer (PBS, BSA 2%, FCS 5%), cells were incubated with primary antibody [1:200 for γ-tubulin antibody (T8328; Sigma) and 1:1000 for γ-tubulin (ab27076; abcam)] in IFF for 45 min at room temperature. Cells were washed with PBS 0.1% Tween and incubated with secondary fluorescent antibody Alexa fluor (Invitrogen) in IFF for 30 min at room temperature. After washing with PBS 0.1% Tween, slides were mounted with Antifade ProLong with DAPI (Invitrogen).

ERCC1-XPF Immunofluorescence Staining

Cells were fixed and permeabilized in formol and SDS 0.1% and then washed with PBS. After blocking with BSA 5%, cells were incubated with primary antibodies (1:200) ERCC1-FL297 (sc-10785; Santa Cruz), XPF-3F2 (ab85140; Abcam) in blocking solution for 1 h at 37° C. Cells were washed with PBS and incubated with secondary fluorescent antibody Alexa fluor (Invitrogen) in blocking solution for 1 h at 37° C. After washing with PBS, slides were mounted with Antifade ProLong with DAPI (Invitrogen).

Proximity Ligation Assay (PLA)

Protein interactions were studied using the Duolink II proximity ligation assays (PLA) kit (Olink, Uppsala, Sweden). Coverslips were processed according to the manufacturer's instructions. In brief, the cells were fixed with methanol, permeabilized with triton, stained with the primary antibodies, and then incubated with the secondary oligonucleotide-linked antibodies. The oligonucleotides were hybridized, ligated, amplified, and detected using a fluorescent probe.

For all IF staining images were acquired an Inverted Ti-E fluorescence microscope (Nikon) and were processed with ImageJ software.

Results

Absence of Negative Dominant Isoform for Cisplatin Sensitivity.

We previously determined that only ERCC1-202 isoform appeared able to allow removal of cisplatin-DNA adducts and to improve survival after cisplatin treatment (Friboulet 2013). Since ERCC1-203 isoform had been proposed to be a negative dominant of ERCC1 DNA repair function, we tried to elucidate what influence could have ERCC1-201, 203 and 204 isoforms on ERCC1-202 DNA repair capacity.

Figure 3A:
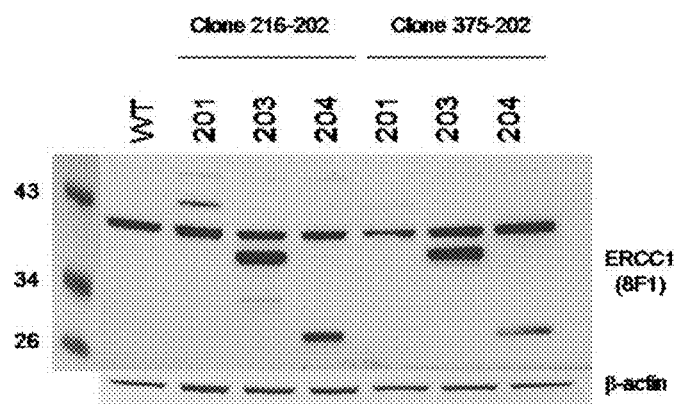
FIG. 3A shows absence of negative dominant isoform—Western Blot detection of ERCC1 isoforms with 8F11 antibody—Cells expressing the 202 isoform were infected with lentivirus coding another ERCC1 isoform.
Figure 3B:
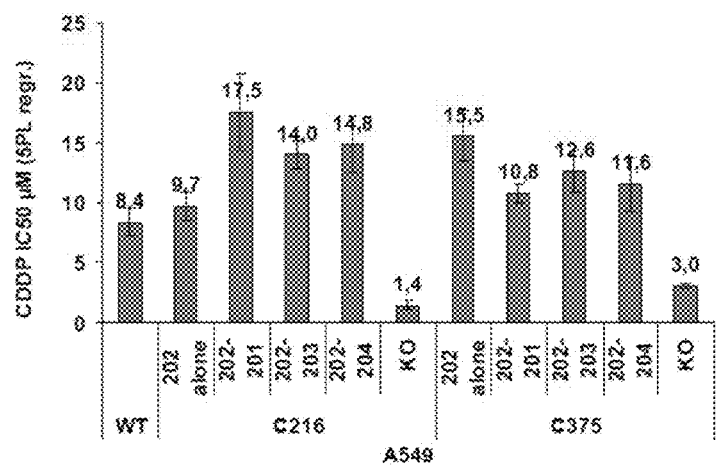
FIG. 3B shows absence of negative dominant isoform—IC50 assessment by WST-1 assay in cells treated for 48 hours with various concentrations of cisplatin.

We selectively re-expressed each isoform with the ERCC1-202 isoform (FIG. 3A). Cell viability analysis after cisplatin exposure in these cells did not bring out any suppressive effect of other isoforms. Indeed, none of the other isoforms decreased cisplatin resistance (IC50) conferred by isoform 202 (FIG. 3B). These data were confirmed by clonogenic growth experiments (FIG. 3C).

Cellular Localization of ERCC1 Isoforms.

It has been shown in XPF mutant cell lines, that ERCC1-XPF was detected in the cytoplasm of cells likely due to protein misfolding (Ahmad, 2010). We thus explored the cellular localization and the protein stability of the different ERCC1 isoforms.

Figure 4:
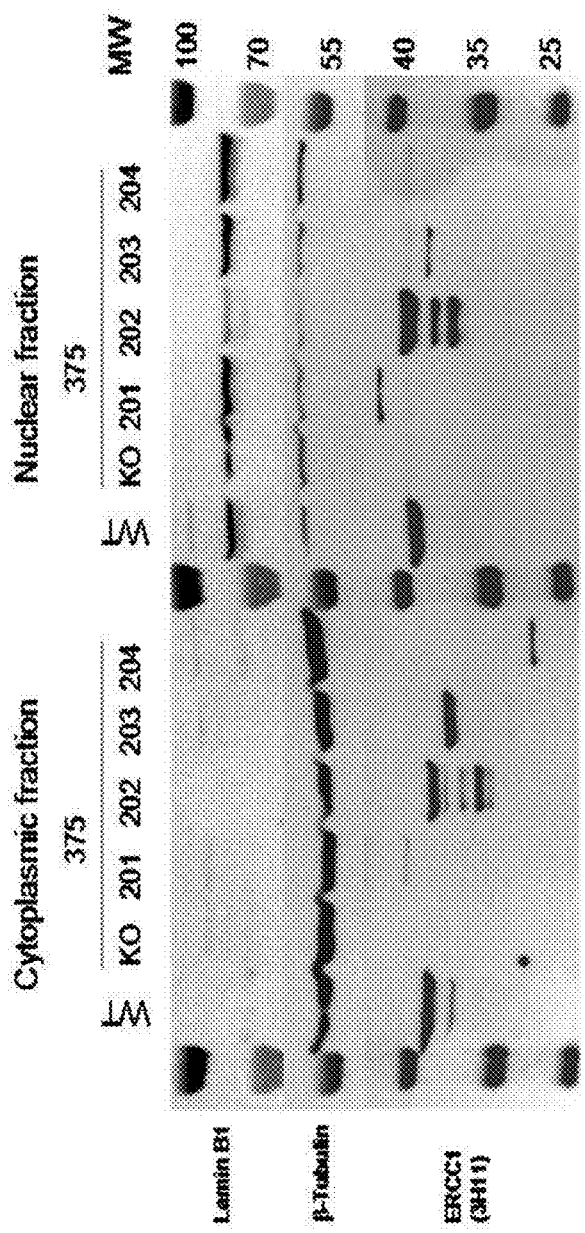
FIG. 4 shows ERCC1 isoforms cellular localization—Western blot detection of ERCC1 protein isoforms after cellular fractionation.

Immunofluorescence detection of ERCC1 protein isoforms suggested a main nuclear localization of ERCC1-201 and -202 isoforms whereas ERCC1-203 and -204 isoform were also detected in the cytoplasm. ERCC1 protein isoforms detection by western blot after cellular fractionation confirmed their differential cellular localization (FIG. 4).

Figure 5A:
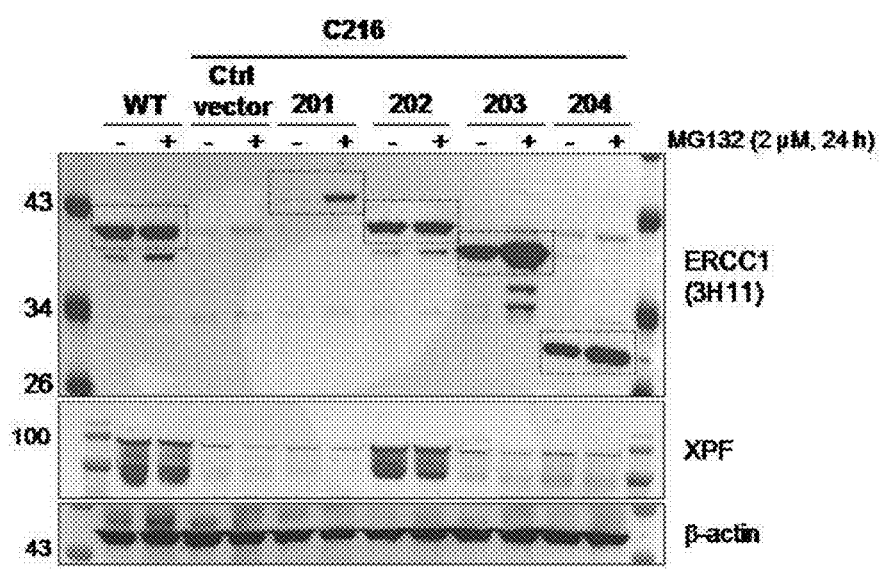
FIG. 5A shows ERCC1 isoforms stability and expression—Western blot detection of ERCC1 protein isoforms after proteasome inhibition (MG132 at 2 µM for 24 h). An increase in ERCC1-201, -203 and -204 expression level suggested instability and degradation of these isoforms.

We thus explored the stability of each protein isoform using proteasome inhibition. This inhibition leaded to an increase expression level of ERCC1-201, -203 and -204 suggesting these isoforms are unstable and quickly degraded probably due to protein misfolding (FIG. 5A). These results could suggest the uselessness of these isoforms for human cells.

ERCC1-201 mRNA Isoform is Upregulated in Tumours Samples.

We previously detected ERCC1 isoforms at the mRNA level in 123 NSCLC patients belonging to the Chemores consortium (Friboulet, 2011). To investigate a possible role of ERCC1 isoforms in the oncogenic process we compared the expression of ERCC1 isoforms between matched tumour and normal specimens by qRT-PCR. The four isoforms were detected at the mRNA level, both in tumor and normal tissues (FIG. 5B). Interestingly, a significant increase in ERCC1-201 isoform expression was observed in all tumor tissues compared to normal counterparts. Other isoforms were homogenously expressed in normal and tumor tissues. This overexpression of ERCC1-201 isoform in tumour samples could suggest an oncogenic role of this isoform.

ERCC1-202 Isoform is Essential for Proper Chromosome Segregation.

Figure 6A:
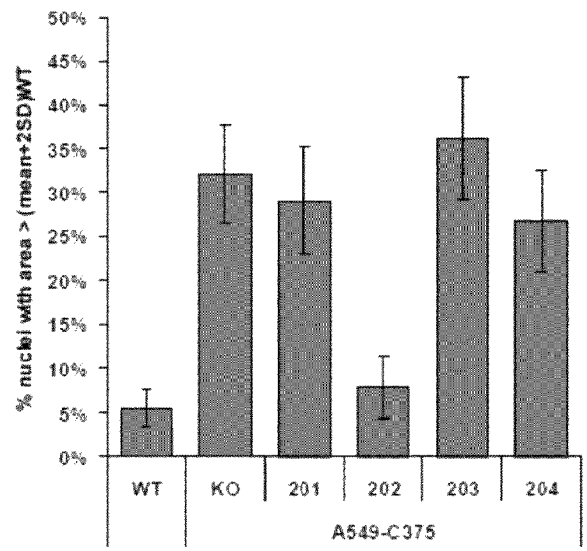
FIG. 6A shows ERCC1-isoform 202 is essential for proper chromosome segregation—Percentage of cells with nucleus size superior of mean of WT nucleus size determined on Diff Quick™ stain cells with ImageJ software.
Figure 6B:
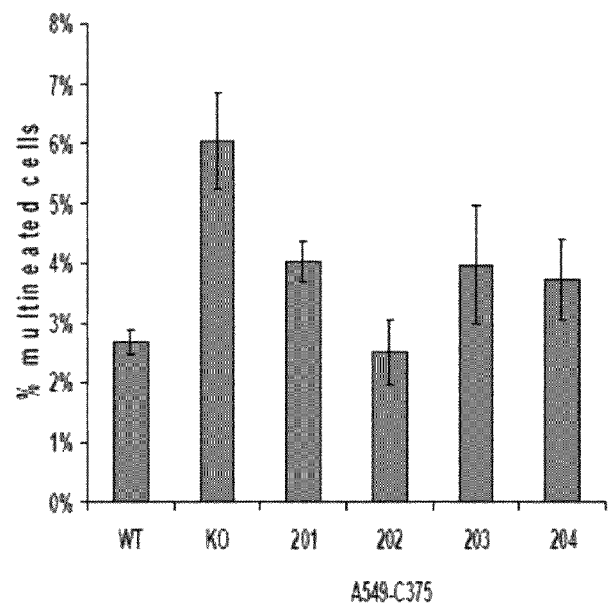
FIG. 6B shows ERCC1-isoform 202 is essential for proper chromosome segregation—Percentage of multi-nucleated cells determined on Diff Quick™ stain cells manually counted (n=200)

Studies reported that ERCC1-deficient mouse cells and human cells after ERCC1 knockdown harboured nuclear and cytoplasm morphologic alterations at least in part due to abnormal mitosis. We indeed observed strong morphologic modifications in ERCC1 deficient cells: bulky cells with huge nucleus, multinucleation and important spreading of the cytoplasm (not shown). We observed these morphologic modifications in cells re-expressing isoforms 201, 203 and 204. Only ERCC1-202 isoform prevented the appearance of cells with giant nucleus and multinucleated cells (FIGS. 6A and 6B).

Figure 6C:
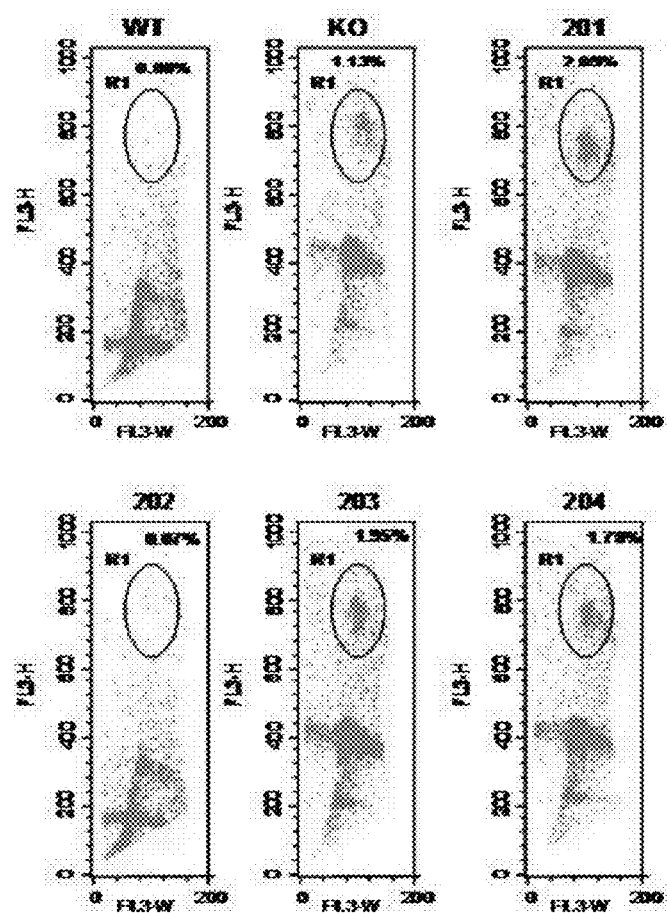
FIG. 6C shows ERCC1-isoform 202 is essential for proper chromosome segregation—DNA content in cells blocked in G2/M cell cycle phase with Karyomax colcemid solution at 0.1 µg/ml for 6 h. Percentages of cells with high DNA content are shown.

Accordingly, by flow cytometry in cells blocked in metaphase by Colcemid microtubule-depolymerizing drug, we observed a significant increase in the percentage of polyploidy cells (more than 4N DNA) in the absence of ERCC1-202 isoform expression (FIG. 6C). After cisplatin treatment (30 and 300 nM for 48 hours) cell lines without ERCC1-202 isoform expression remained largely (60-80%) blocked in G2/M cell cycle phase (not shown). Altogether, these data confirmed that the ERCC1 functional-deficiency may induce aneuploidy.

Figure 6D:
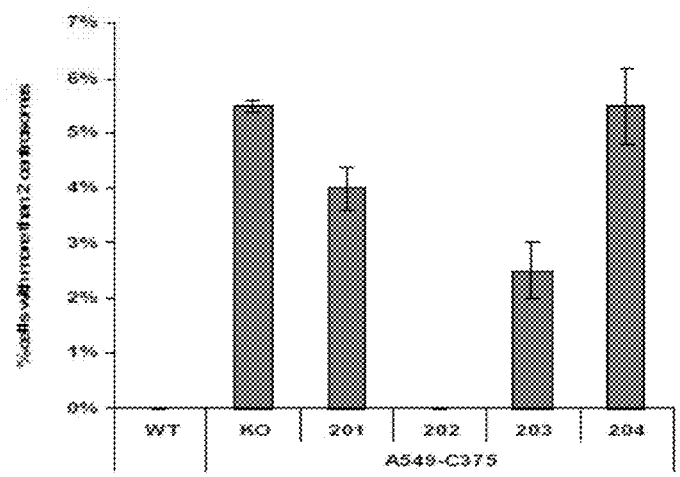
FIG. 6D shows ERCC1-isoform 202 is essential for proper chromosome segregation—ERCC1 WT, attenuated and rescued cells. Centrosomes (-tubulin) were manually counted (n=100). Percentages of cells with more than 2 centrosomes are shown.
Figure 6E:
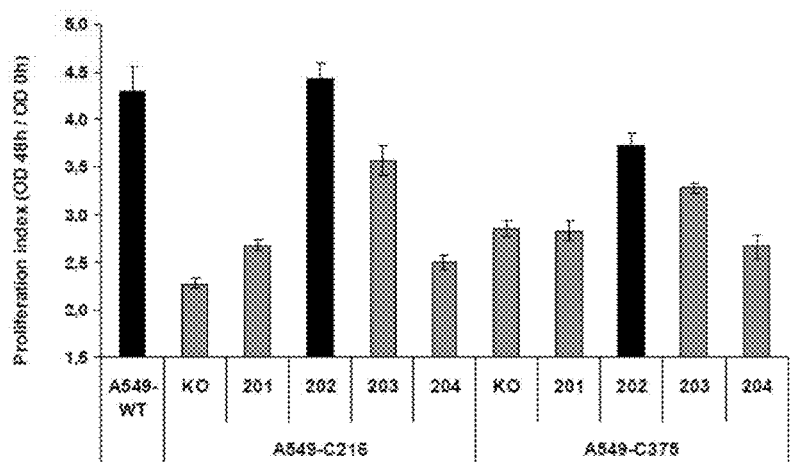
FIG. 6E shows ERCC1-isoform 202 is essential for proper chromosome segregation—E) 48 hours proliferation index in untreated ERCC1 WT, attenuated and rescued cells determined by WST-1 assay.

Improper chromosomes alignment for metaphase was proposed to explain multinucleation occurrences in ERCC1 attenuated cells. We analysed mitotic spindle shape in proliferating cells by alpha- and gamma-tubulin immunofluorescent staining. We observed abnormal centrosomes number and many DNA bridges in cells without ERCC1-202 isoform expression (FIG. 6D). DNA bridges have been shown to occlude the division site and are a common cause for cytokinesis failure. It is therefore possible that the increase in DNA bridges observed in ERCC1-deficient cells leads to a failure in cell division. By monitoring the cell division in time-laps experiments, we indeed observed impaired cytokinesis leading to daughter cells fusion (not shown). Accordingly, these mitosis defects reduced strongly the proliferation rate in cells without ERCC1-202 isoform expression (FIG. 6E). Our results clearly suggested that only ERCC1-202 isoform restored chromosome segregation accuracy.

ERCC1 Isoforms Function in ICL-R and HR.

Figure 7:
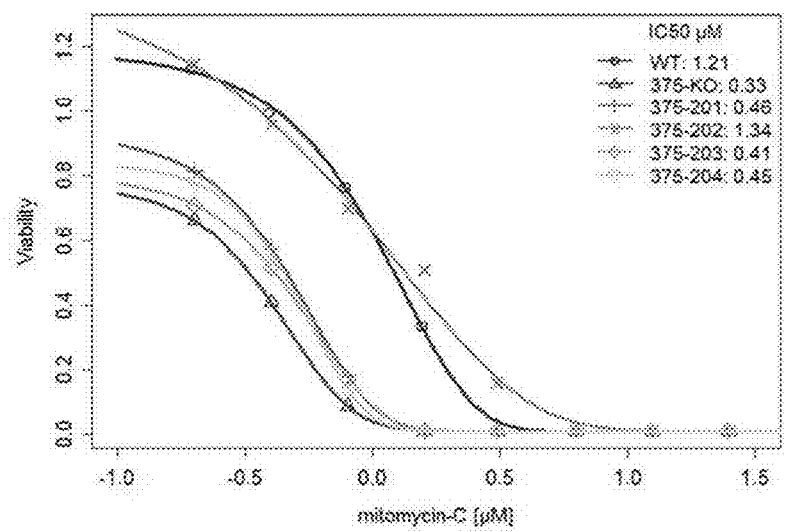
FIG. 7 shows ERCC1 isoforms function in ICL-R-IC50 assessment by WST-1 assay in cells treated for 48 h with various concentrations of the DNA interstrand cross-linking agent mitomycin-C. MMC IC50 (µM) values are indicated for each clone. Only 202 isoform restored MMC resistance compared to WT cells.

It is clearly established that Fanconi anemia (FA) pathway-deficient cells are hypersensitive to DNA crosslinking agent such as mitomycin C (MMC). More recently, it has been shown that disruption of the FA pathway results in cytokinesis failure with frequent DNA bridges and an increase in multinucleated cells (Vinciguerra, 2010). It can be speculated that cytokinesis failure observed in ERCC1-deficient cells could arise from defect in ICL-R. We therefore investigated the ICL-R ability of the different ERCC1 isoforms by determining the mitomycin-C IC50-values of cells expressing unique isoform. As we previously observed for cisplatin treatment, MMC cell resistance was rescued only by ERCC1-202 isoform re-expression in short term (48 h) proliferation assays (FIG. 7). It is therefore possible that unrepaired ICL damage in ERCC1-202 deficient cells lead to DNA bridges and cytokinesis failure.

By immunofluorescence we analysed the amount of H2AX and Rad51 foci after mitomycin-C treatment.

Accordingly, we observed an increase in ERCC1-202 isoform expression (not shown).

Interacting Abilities of ERCC1 Isoforms

Studies suggested that ERCC1 and XPF are unstable in the absence of each partner in mammalian cells (Arora, 2010). Indeed in our ERCC1-deficient cells the expression level of XPF was highly reduced (FIG. 5A). We noticed that only ERCC1-202 isoform expression rescued XPF protein expression levels. Considering many works that proposed ERCC1/XPF as a necessary complex to ensure stability of both proteins we speculated that only isoform 202 was able to interact with and protect against XPF degradation.

Figure 8A:
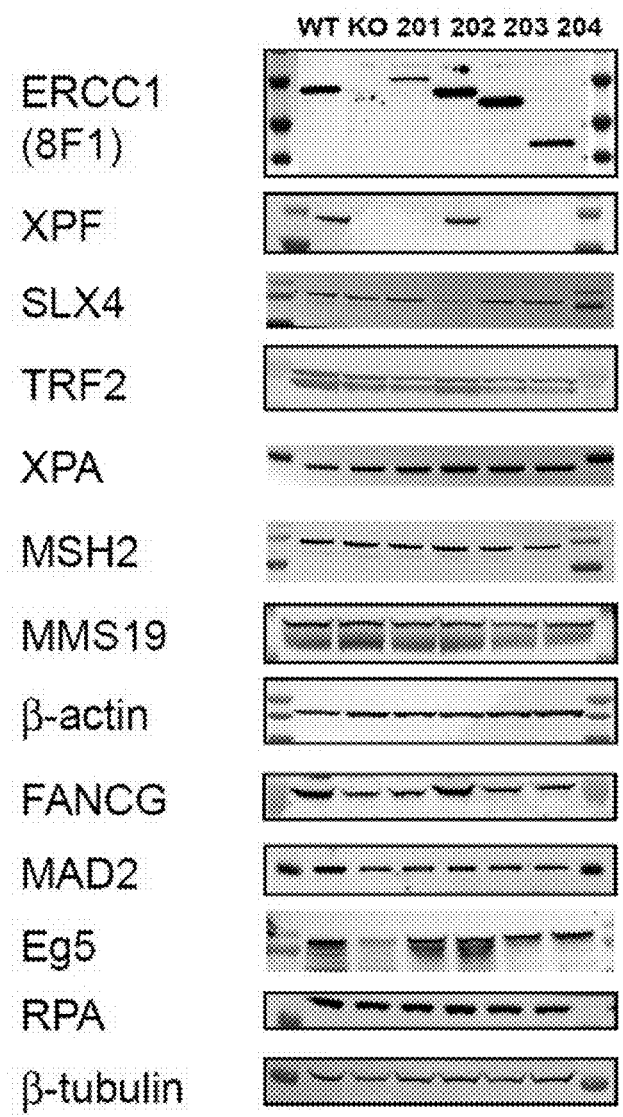
FIG. 8A shows ERCC1-protein complexes required ERCC1-202 isoform expression—Western blot detection of ERCC1 protein isoforms and ERCC1 interacting proteins.

The expression level of others previously described ERCC1 interacting proteins was analyzed in cells expressing only one ERCC1 isoform. Loss of ERCC1 expression and isoform expression rescue did not modify the protein expression level of XPA, SLX4, TRF2, FANCG, MAD2A, Eg5 or MSH2 proteins (FIG. 8A).

Using proximity ligation assays (PLA-Duolink) technology, we investigated the binding ability of ERCC1 isoforms with ERCC1 interacting proteins. High number of ERCC1/XPF heterodimers were detected only in cells expressing ERCC1-202 isoform (FIG. 8B). These data provided evidence that XPF protein is unstable in the absence of ERCC1-202 isoform and that only this isoform could form a stable heterodimer complex with XPF.

Figure 8C:
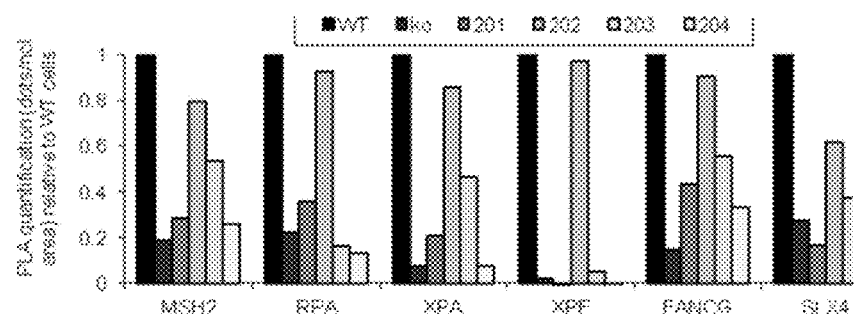
FIG. 8C shows ERCC1-protein complexes required ERCC1-202 isoform expression—Proximity ligation assay (PLA-Duolink) detection of ERCC1/XPF, ERCC1/XPA, ERCC1/MSH2, ERCC1/FANCG, ERCC1/SLX4, ERCC1/Eg5, ERCC1/MAD2A, ERCC1/SLX4 and ERCC1/TRF2 heterodimers definite the unique binding ability of ERCC1-202 isoform only. ERCC1 was detected using FL297 antibody.

Similarly, we identified ERCC1/XPA, ERCC1/MSH2, ERCC1/FANCG, ERCC1/SLX4, ERCC1/Eg5, ERCC1/MAD2A and ERCC1/TRF2 complexes only with ERCC1-202 isoform (FIG. 8C). All together these data suggested that ERCC1-protein complexes required ERCC1-202 isoform expression.

Discussion

Despite the huge interest of ERCC1 biomarker in the cancer research community, the DNA repair functionality and alternative roles of the different human ERCC1 isoforms remained largely uncharacterized. In order to study ERCC1 isoforms individually we established the first ERCC1 knockout NSCLC cell lines (Friboulet NEJM 2013).

For the first time we brought out that several previously identified functions of ERCC1 are realized by the same ERCC1 isoform, the ERCC1-202. We have shown that ERCC1 201, 203 and 204 isoforms were unable to achieved ERCC1 functions and interactions and none of them seemed to be a negative dominant of the ERCC1-202 isoform for cisplatin DNA damage repair. The reason for a difference from previous studies proposing a negative role of ERCC1-203 isoform is not known but could be due to a difference in experimental methods used and the fact that completely abolished ERCC1 basal expression appeared essential in our hands to elucidate the biological influence of each isoform.

XPF is essential for the nuclease activity of the ERCC1/XPF complex. Since only ERCC1-202 isoform formed heterodimer with XPF, all functions of the complex linked to nuclease activity can only be observed in cells expressing ERCC1-202 isoform. Other isoforms could be implicated in non-nuclease linked activities but further work is needed to elucidate the specific biological function of each of the other ERCC1 isoforms that seemed to be widely expressed in human samples. The role of specifically overexpression of 201 isoform mRNA in tumors also remains to be clarified.

Cells deficient in ERCC1 protein displayed high rates of multinucleated cells as a result of DNA bridges and cytokinesis failure. It has been speculated that unrepaired DNA damages may be the source of elevated chromatin bridges and cytokinesis failure. We can therefore hypothesize that ERCC1 implication in mitosis could at least in part account for the nuclease activity of the ERCC1/XPF complex in DNA repair.

Our data clearly suggested that the development of a diagnostic method recognizing ERCC1/XPF heterodimers should match to functional ERCC1-202 isoform quantification only.

We claim:

1. An in vitro method for measuring an expression level of an isoform 202 of an ERCC1 protein in a tumor cell, said method comprising the step of performing an immunohistochemistry assay on a formalin-fixed paraffin-embedded tumor sample, wherein said tumor cell is suspected of being susceptible to a platinum-based chemotherapy.

2. The method according to claim 1, wherein said immunohistochemistry assay uses a monoclonal ERCC1 antibody recognizing specifically the isoform 202 of the ERCC1 protein or an antibody recognizing specifically isoform 202 of the ERCC1 protein in a complex selected from the group consisting of: ERCC1/XPF, ERCC1/XPA, ERCC1/MSH2, ERCC1/FANCG, ERCC1/SLX4, ERCC1/Eg5, ERCC1/MAD2A, and ERCC1/TRF2.

3. The method according to claim 1, further including the steps of:
   (a) obtaining slides from formalin-fixed paraffin-embedded tumor samples;
   (b) retrieving epitope in buffer;
   (c) incubating slides with a monoclonal ERCC1 antibody recognizing specifically the isoform 202 of the ERCC1 protein; or with an antibody recognizing isoform 202 of the ERCC1 protein in a complex selected from the group consisting of: ERCC1/XPF, ERCC1/XPA, ERCC1/MSH2, ERCC1/FANCG, ERCC1/SLX4, ERCC1/Eg5, ERCC1/MAD2A, and ERCC1/TRF2;
   (d) determining an amount of binding antibodies on the formalin-fixed paraffin-embedded tumor samples, using the amount of binding antibodies on an internal positive control as a reference;
   (e) determining a percentage of labeled nuclei on the formalin-fixed paraffin-embedded tumor samples;
   (f) multiplying the value estimated in step (d) with the value estimated in step (e); and
   (g) determining a platinum-based chemotherapy regimen by comparing the value obtained in step (f) to a median score of the values obtained in step (f).

4. The method according to claim 3, wherein the internal positive control consists of stroma cells surrounding the tumor area.

5. The method according to claim 1, wherein said expression level is measured by means of an antibody that recognizes specifically the isoform 202 of the ERCC1 protein; or with an antibody recognizing specifically isoform 202 of the ERCC1 protein in a complex selected from the group consisting of: ERCC1/XPF, ERCC1/XPA, ERCC1/MSH2, ERCC1/FANCG, ERCC1/SLX4, ERCC1/Eg5, ERCC1/MAD2A, and ERCC1/TRF2.

6. The method according to claim 1, wherein said tumor is a non-small-cell lung cancer.

7. The method according to claim 1, wherein said chemotherapy is cisplatin with etoposide or a *vinca* alkaloid.

8. The method according to claim 1, wherein said patient had undergone a surgical resection of its tumor.

9. An in vitro method for measuring an expression level of an isoform 202 of an ERCC1 protein in a tumor cell, said method comprising the step of performing an immunofluorescence assay performed on individual tumor cells, wherein said tumor cell is suspected of being susceptible to a platinum-based chemotherapy.

* * * * *